United States Patent
Kim et al.

(10) Patent No.: US 9,504,725 B2
(45) Date of Patent: Nov. 29, 2016

(54) COMPOSITIONS AND FUNCTIONAL FOODS FOR TREATING AND PREVENTING OBESITY USING POLYGONUM CUSPIDATUM BUTANOL FRACTION AND ETHYL ACETATE FRACTION

(75) Inventors: Jin Sook Kim, Seoul (KR); Dae Sik Jang, Daejeon (KR); Young Sook Kim, Daejeon (KR); Junghyun Kim, Seoul (KR); Chan-Sik Kim, Daejeon (KR)

(73) Assignee: KOREA INSTITUTE OF ORIENTAL MEDICINE, Daejeon (KR)

( * ) Notice: Subject to any disclaimer, the term of this patent is extended or adjusted under 35 U.S.C. 154(b) by 0 days.

(21) Appl. No.: 13/498,247

(22) PCT Filed: Dec. 29, 2009

(86) PCT No.: PCT/KR2009/007911
§ 371 (c)(1),
(2), (4) Date: Mar. 26, 2012

(87) PCT Pub. No.: WO2011/081231
PCT Pub. Date: Jul. 7, 2011

(65) Prior Publication Data
US 2012/0183633 A1    Jul. 19, 2012

(51) Int. Cl.
*A61K 36/704*    (2006.01)

(52) U.S. Cl.
CPC ............ *A61K 36/704* (2013.01); *A23L 33/105* (2016.08)

(58) Field of Classification Search
None
See application file for complete search history.

(56) References Cited

U.S. PATENT DOCUMENTS

2008/0292689 A1* 11/2008 Row et al. .................. 424/450

FOREIGN PATENT DOCUMENTS

| CN | 1302610 A | | 7/2001 |
|---|---|---|---|
| CN | 1450077 A | * | 10/2003 |
| CN | 101433598 A | | 5/2009 |
| JP | 2004075638 A | * | 3/2004 |
| JP | 2006273834 A | | 10/2006 |
| KR | 10-1993-0001890 A | | 2/1993 |
| KR | 10-2004-0045604 A | | 12/2005 |
| KR | 10-0824970 B1 | | 4/2008 |
| KR | 10-2008-0088163 A | | 10/2008 |
| KR | 10-2009-0125726 A | | 12/2009 |
| KR | 10-2010-0002658 A | | 1/2010 |
| WO | 2008092221 A2 | | 8/2008 |

OTHER PUBLICATIONS

Stroud, L. M. "Substitution of a more hazardous chemical by a less hazardous chemical". Internet date: 2008 [Retrieved from the Internet on: May 21, 2014]. Retrieved from: <URL: http://www.sciencesafetyconsulting.com/pdf/chemical_substitutions.pdf>.*
Enns, G. "Metabolic disease". [Retrieved from the Internet on: Jun. 15, 2015]. Retrieved from: <URL: http://www.britannica.com/science/metabolic-disease>.*
Mayo clinic staff. "Goucher's disease". May 13, 2014 [Retrieved from the Internet on: Jun. 14, 2015]. Retrieved from: <URL: http://www.mayoclinic.org/diseases-conditions/gauchers-disease/basics/treatment/con-20031396?p=1>.*
Kim, Yeong Hun, et al., "Study on Anti-oxidant Activity of Four Kinds of Korea Herb Medicine Materials", Journal of the Korean Society of Fashion & Beauty, 5(4): 139-144, 2007.
Kim, Dong Jo, et al., "Endothelium Dependent Vasorelaxant Effect of Aqueous Extract of Polygoni Cuspidatae Radix on Arterial Contraction in Rabbit", Korean J. Oriental Physiology & Pathology, 22(1): 131-136, 2008.
Na, Minkyun; et al. "Protein Tyrosine Phosphatase 1B Inhibitory Activity of Anthraquinones and Stilbenes", S. Korea Natural Product Sciences (2008), 14(2), 143-146, Abstract only.
J. Kim, et al. "POCU1b reverses diabesity induced in rats fed high-fat diet" Planta Med 2009; 75-SL32, DOI: 10.1055/s-0029-1234287.
Bret C. Vastano et al. "Isolation and Identification of Stilbenes in Two Varieties of Polygonum cuspidatum" J. Agric. Food Chem. 2000, 48, 253-256.

* cited by examiner

*Primary Examiner* — Amy L Clark
(74) *Attorney, Agent, or Firm* — Norton Rose Fulbright US LLP

(57) ABSTRACT

The present invention relates to the obesity-curative or obesity-preventive effect of a *Polygonum cuspidatum* butanol fraction and a *Polygonum cuspidatum* ethylacetate fraction, and more particularly, to a pharmaceutical composition and a functional food for treating obesity, the pharmaceutical composition and the functional food comprising a *Polygonum cuspidatum* butanol fraction (POCU-1b) and an ethylacetate fraction as active ingredients, wherein the *Polygonum cuspidatum* butanol fraction and the ethylacetate fraction inhibit effectively the activity of pancreatic lipase, an important enzyme involving in fat absorption in a living body, and have excellent inhibitory effect on fat absorption in the short term fat absorption-inhibitory animal experiments using lipid emulsions.

3 Claims, 54 Drawing Sheets

COMPOSITIONS AND FUNCTIONAL FOODS FOR TREATING AND PREVENTING OBESITY USING POLYGONUM CUSPIDATUM BUTANOL FRACTION AND ETHYL ACETATE FRACTION

CROSS-REFERENCE TO RELATED APPLICATION

This application is a 371 of PCT/KR2009/007911, filed Dec. 29, 2009, the contents of which are incorporated herein by reference.

TECHNICAL FIELD

The present disclosure relates to fractions obtained from systematic fractionation of *Polygonum Cuspidatum* extracts, which can be applied to pharmaceutical compositions and functional foods for preventing and treating obesity.

BACKGROUND

Obesity is a condition in which excess energy has accumulated as a fat in the body as a result of energy intake being greater than energy expenditure. According to the 2005 Korea National Health and Nutrition Examination Survey, the prevalence of obesity among Korean adults aged 20 years and older was 31.8% and it has increased by more than double from 14.8% in 1995 during the past 10 years (Ministry of Health & Welfare. 2006. The third Korea National Health and Nutrition Examination Survey). Due to this increasing tendency, the socioeconomic loss caused by obesity has increased annually from 1,700 billion won in 2001 and the government has set a main objective to maintain the prevalence of adult obesity of around 30% by 2010 in Health Plan (Ministry of Health & Welfare. 2005. Health Plan. pp. 61-64). Since obesity not only has its own problems, but it can also cause diseases such as cardiovascular diseases, diabetes, respiratory diseases, or osteoarthritis, much attention has been focused on obesity from around the world (Antipatis V. J. et al., 2001, Obesity as a global problem. In *International textbook of obesity*. Per Bjorntorp, ed. John Wiley & Sons Ltd, Chichester, UK. pp. 3-22) and World Health Organization deals with obesity as a global nutritional problem and recognizes it as a disease that should be treated, not a simple risk factor that damages health (World Health. 1998. Obesity: Preventing and managing the global epidemic. Report of WHO Consultation on Obesity, Geneva). Obesity is caused by a combination of excessive energy intake, lack of physical activity as well as secretory factors in the nerve system, medications, genetic factors, etc. and diet, physical exercise, behavior modification therapy, drug treatments, etc. are used for relieving obesity.

Recently, a lot of research on developing therapeutic agents for obesity has been made and one of such research is about pancreatic lipase inhibitors. Pancreatic lipase is a key enzyme which degrades triglycerides into 2-monoacylglycerol and fatty acids (Bitou N. et al., 1999, *Lipid* 34:441-445) and a currently known representative pancreatic lipase inhibitor is tetrahydrolipstatin (orlistat), a derivative of lipstatin derived from *Streptomyces toxitricini*. Orlistat (Xenical) which is now commercially available as a drug has been known to be one of the most efficient pancreatic lipase inhibitors enough to prevent the absorption of approximately 30% dietary fat (Drent M. et al., 1995, *Int. J. Obesity.* 19:221-226). Despite this, orlistat has been known to have side effects such as gastrointestinal problems, hypersensitivity, dyscholia, inhibition of the absorption of fat-soluble vitamins, etc. (Peter C. et al., 2001, *Br. J. Clin. Pharmacol.* 51:135-141). According to FDA guidelines for weight-loss treatment, anti-obesity drugs for long-term use should result in a efficacy of 5% weight loss from the weight before administration of the drugs and the weight-loss effect should be maintained for at least 12 months. However, after two years of long-term administration of orlistat, the weight loss was merely 3 to 5% compared to a diet alone and the side effect of inhibiting the absorption of fat-soluble vitamins A, D, and E was showed. Orlistat was released in 1998 and sales were $900,006,300 in 2001, however, had since slowed owing to such side effect and poor efficacy. Thus, research has recently been performed on developing pancreatic lipase inhibitors from foods and natural products which have no side effects (Yamamoto M. et al., 2000, *Int. J. Obesity.* 24:758-764).

Anti-obesity materials developed using natural products are classified into categories by mechanisms of action, namely those which: involve in suppressing appetite; inhibit fat digestion and absorption; induce heat generation and inhibit fat accumulation; and regulate lipid metabolism. Examples of those which involve in suppressing appetite include hydroxycitric acid (HCA), Olibra, dietary fibers such as chicory and inulin. Examples of those which inhibit fat digestion and absorption include chitosan, flavonoids, etc. Examples of those which induce heat generation and inhibit fat accumulation include capsaicin in chili peppers, catechin in green tea, retinoic acids, etc. L-carnitine, conjugated linoleic acid (CLA), calcium in milk and related proteins are reported for examples of those which regulate lipid metabolism. Examples of medicinal herbs which have effect on weight control include poncirus, Zingiber mioga, Cassia tora, green tea, pine needles, sophora, cnidium, evodia, etc. (Kim M. H., 2004, *Korean J. Heath Psychol.* 9:493-509, Reddy P. et al., 1998, *Formulary* 33:943-959, Burns A. A. et al., 2002, *Eur. J. Clin. Nutr.* 56:368-377, Delzenne N. M. et al., 2005, *Br. J. Nutr.* 1:157-161, Zacour A. C. et al, 1992, *J. Nutr. Sci. Vitamilol.* 38:609-613, Griffiths D. W. et al., 1986, *Adv. Exp. Med. Biol.* 1999:509-516). Consumers have great interests in therapeutic agents made from natural materials which have little side effects, but have excellent medicinal efficacy and accordingly, in order to meet the demand, there is need for developing safe and highly efficient natural remedies.

Meanwhile, *Polygonum cuspidatum* Sieb. et Zucc. (=*Reynotria japonica* Houtt.) is a member of the Polygonaceae family, an herbaceous perennial, having a thick rhizome and stems of approximately 1.5 m in height. Leaves are alternate, oval, about 6 to 12 cm in length, pointed at the tip, and leaves are on long petiole. Flowers are dioecism, bloom in June to August. Fruits are achene, triangular oval, and glossy dark brown. It grows in mountain valleys throughout the country and is distributed in Japan, China, and Taiwan (Bae Gihwan, Medicinal plants of Korea, Kyohak Publishing Co., Ltd., 2003, p. 89). Rhizomes and roots of *Polygonum cuspidatum* are called as *Polygonum cuspidatum* or *Polygoni Rhizoma* (=*Reynoutriae Rhizoma*) and included in the medium grade of wood section from Bencao Gangmu (Compendium of Materia Medica). In Korean folk medicine, it has been used as a palliative and diuretic and in the treatment of pyodermatitis, cystitis, cancers, etc. and in Chinese medicine, it has been used for expelling wind dampness, breaking blood stasis, treating menorrhalgia, relieving cough and relieving spasm (Yuk Changsu, Illustrated Guide to Asian Herbal Medicine, Kyungwon Publishing Co., Ltd., 1997, p. 140; Ji Okpyo, 1975, Korean Journal of Pharmacognosy, 6:1-4). Reported its medical actions include inhibition of lipid metabolism (Masaki H., et al., 1995, Biol. Pharm. Bull. 18:162-166, 1995), inhibition of protein tyrosine kinase (Jayatilake G. S., et al., 1993, *J. Nat. Prod.* 56: 1805-1810), inhibition of mutagenicity (Su et al., 1995, *Mutat. Res.* 329:205-212), etc. It has been known that its main components are stilbenes, anthraquinone, and glycosides thereof, including polydatin, resveratrol, emodin, physcion, and chrysophanoic acid (Pan et al., 2000, *Zhong Yao Cai*, 23: 56-58; Zhang, 1999, *Tianjin Yi Yao*, 11:13-14). However, research on its fractions has not yet been conducted so far and there has been no report that the fractions are effective in treating and preventing obesity.

Thus, the present inventors have tried to develop an agent for treating and preventing obesity using natural drugs and found that fractions of *Polygonum Cuspidatum* extracts are effective in inhibiting pancreatic lipase activity and fat absorption, thereby leading to completion of the present invention.

DISCLOSURE OF THE INVENTION

Technical Problem

One object of the present invention is to provide a pharmaceutical composition for preventing or treating obesity being effective in: inhibiting the activity of pancreatic lipase, an important enzyme involving in excess energy intake, especially, fat absorption, being one of major causes of obesity; inhibiting short term fat absorption using lipid emulsions; and inhibiting body weight gain and reducing body weight in high-fat diet-induced obesity.

Another object of the present invention is to provide a pharmaceutical composition and a functional food for preventing and treating hyperlipidemia or metabolic diseases.

Still another object of the present invention is to provide a method of preventing or treating obesity.

Even another object of the present invention is to provide a use of a butanol fraction or an ethylacetate fraction of a *Polygonum cuspidatum* extract for preparation of a composition for preventing or treating obesity.

Technical Solution

In order to achieve the objects, the present invention provides a composition for treating and preventing obesity comprising an ethylacetate fraction or a butanol fraction as an active ingredient, wherein the ethylacetate fraction or the butanol fraction is obtained by stepwise fractionating a *Polygonum cuspidatum* extract with hexane, ethylacetate, and butanol, in which the *Polygonum cuspidatum* extract is extracted with an alcohol, water, or a mixture thereof.

The present invention also provides a method of preventing and treating obesity using the fraction.

Furthermore, the present invention provides a health functional food for preventing and relieving obesity comprising the fraction as an active ingredient.

Advantageous Effects

*Polygonum cuspidatum* fractions are natural extracts and thus, less toxic and safer than conventional medications for obesity. In addition, the pancreatic lipase activity of *Polygonum cuspidatum* fractions is very effective compared to *Polygonum cuspidatum* extracts or a compound extracted from *Polygonum cuspidatum*, resveratrol and the inhibitory effect on short-term fat absorption, the inhibitory effect on body weight gain, and the reducing effect of body weight of *Polygonum cuspidatum* fractions are more excellent than those of *Polygonum cuspidatum* extracts or resveratrol. Thus, *Polygonum cuspidatum* fractions can be used for a pharmaceutical composition for preventing and treating obesity and a health functional food for relieving obesity.

NOR: control; HFD: high-fat diet; Xen: Xenical (positive control); POCU: *Polygonum cuspidatum* butanol fraction.

Figure 3:
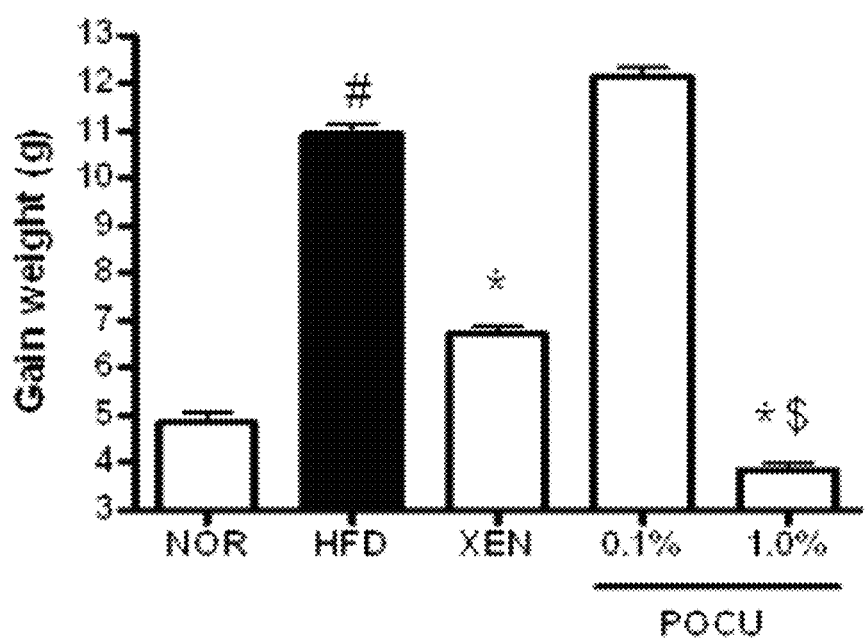

FIG. 3 shows the body weight increment for examining the preventive effect of a *Polygonum cuspidatum* butanol fraction on obesity.

Figure 4:
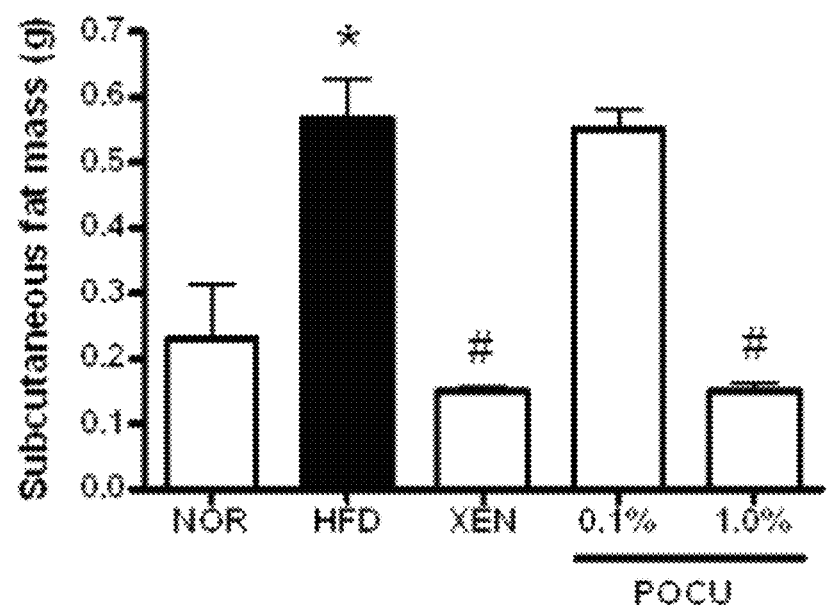

FIG. 4 shows the preventive effect of a *Polygonum cuspidatum* butanol fraction on increases in subcutaneous fat:

NOR: control; HFD: high-fat diet; Xen: Xenical (positive control); POCU: *Polygonum cuspidatum* butanol fraction.

Figure 5:
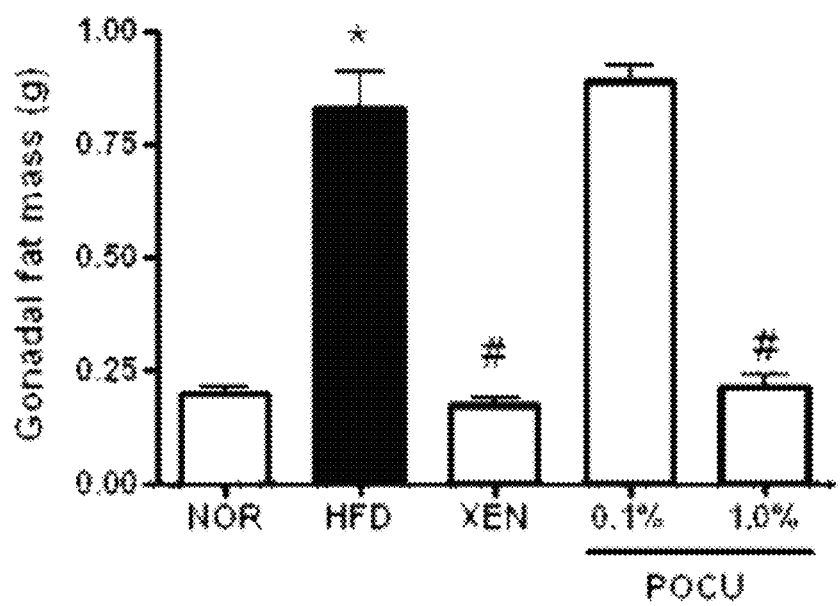

FIG. 5 shows the preventive effect of a *Polygonum cuspidatum* butanol fraction on increase in gonadal fat.

Figure 6:
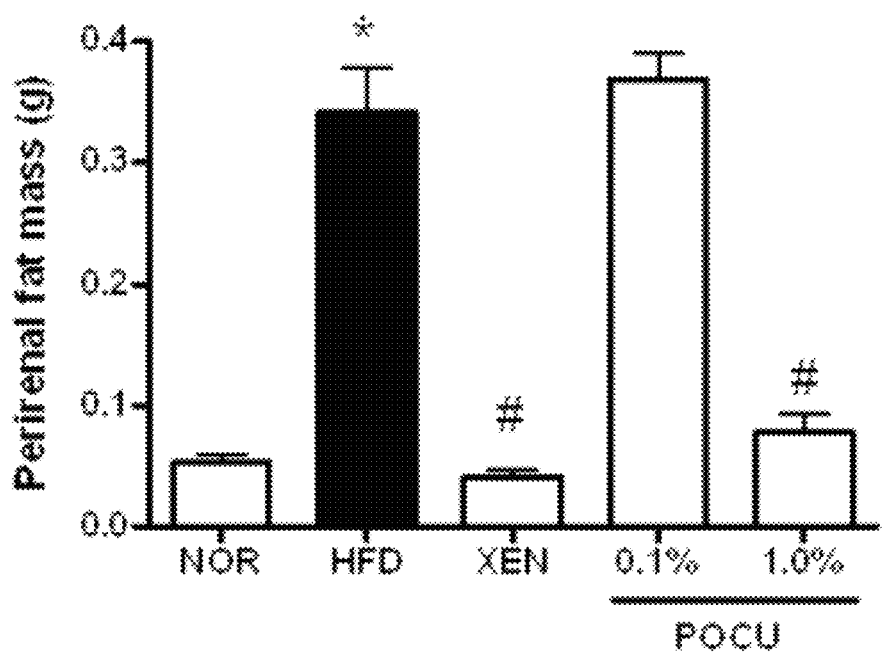

FIG. 6 shows the preventive effect of a *Polygonum cuspidatum* butanol fraction on increase in perirenal fat.

Figure 7:
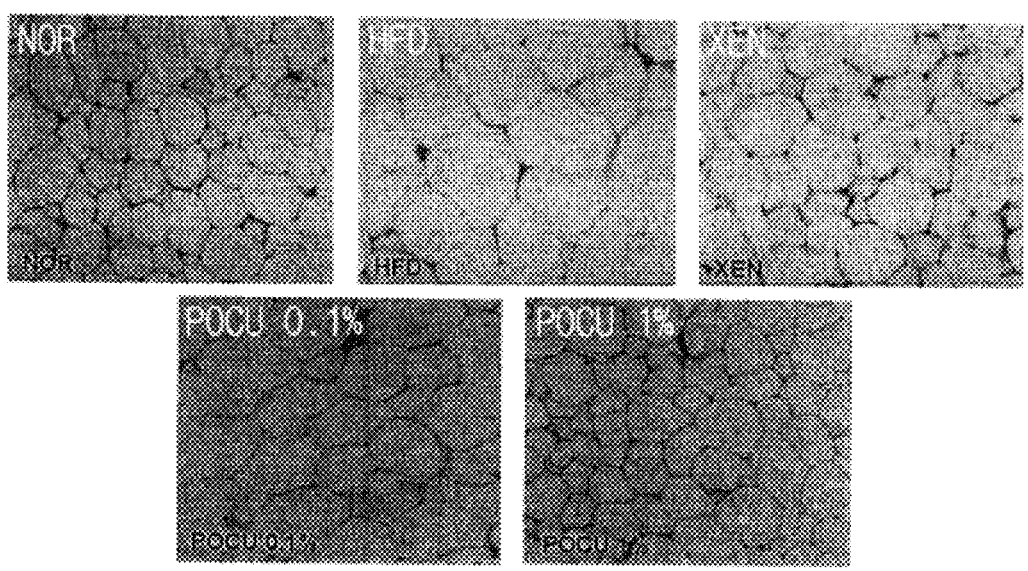
Figure 8:
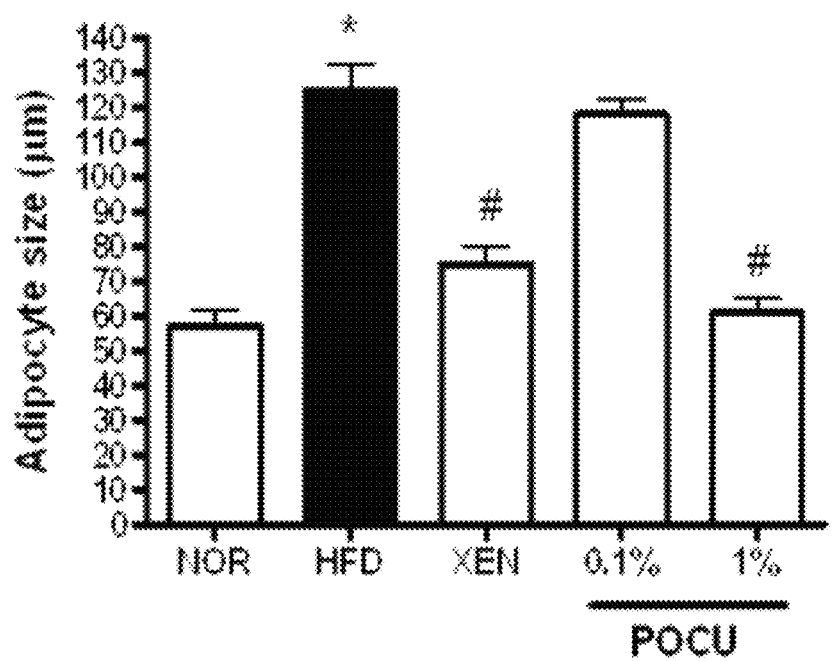

FIGS. 7 and 8 are photographs and a graph illustrating changes in adipocyte size, which are for the observation of the preventive effect on obesity after a *Polygonum cuspidatum* butanol fraction treatment.

Figure 9:
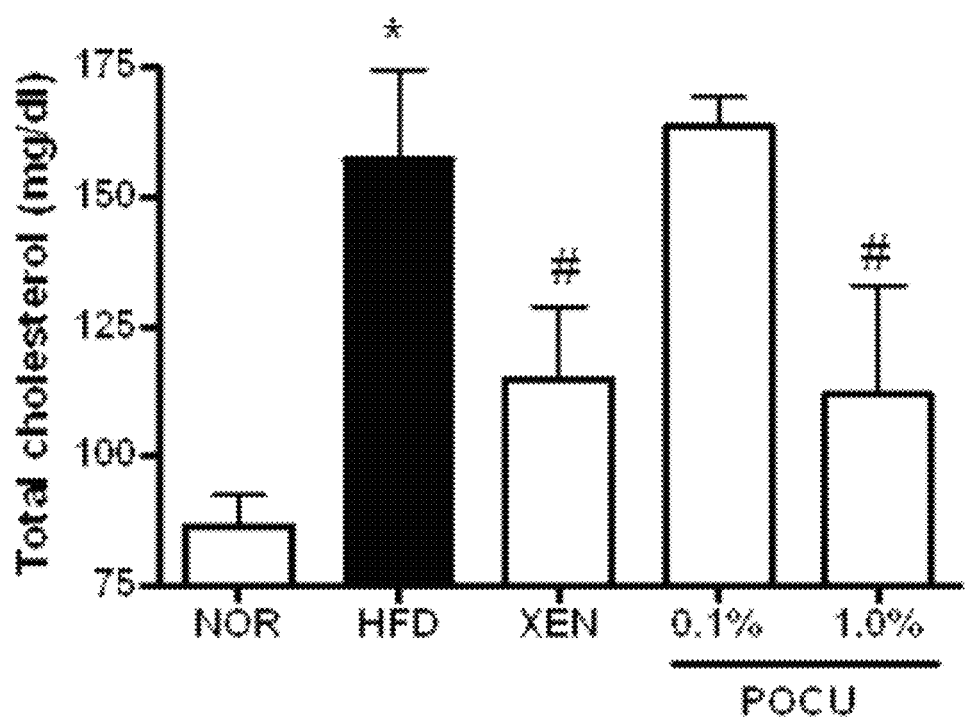
Figure 10:
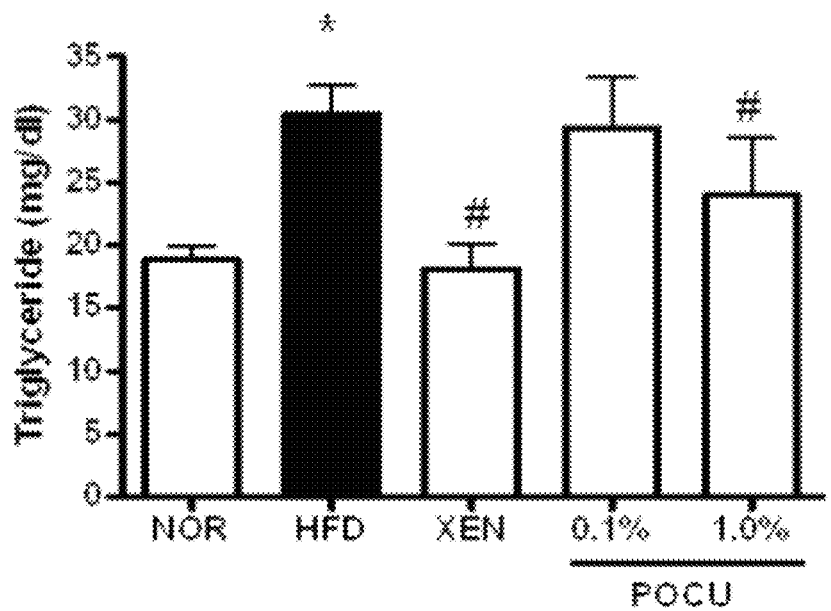
Figure 11:
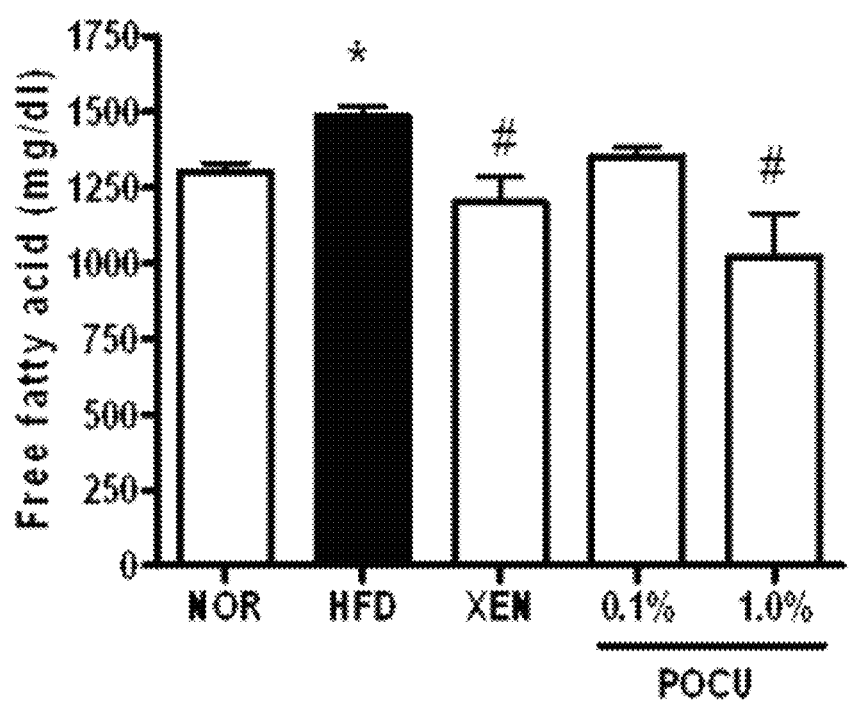
Figure 12:
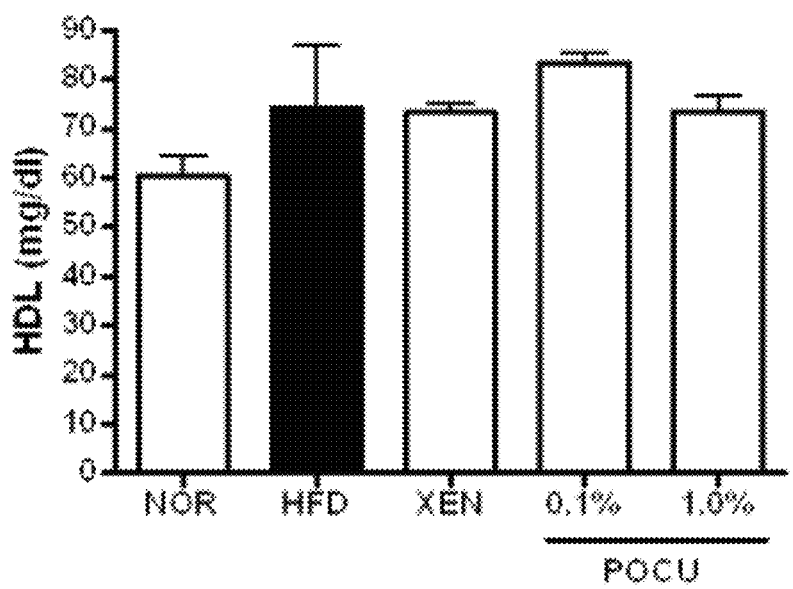
Figure 13:
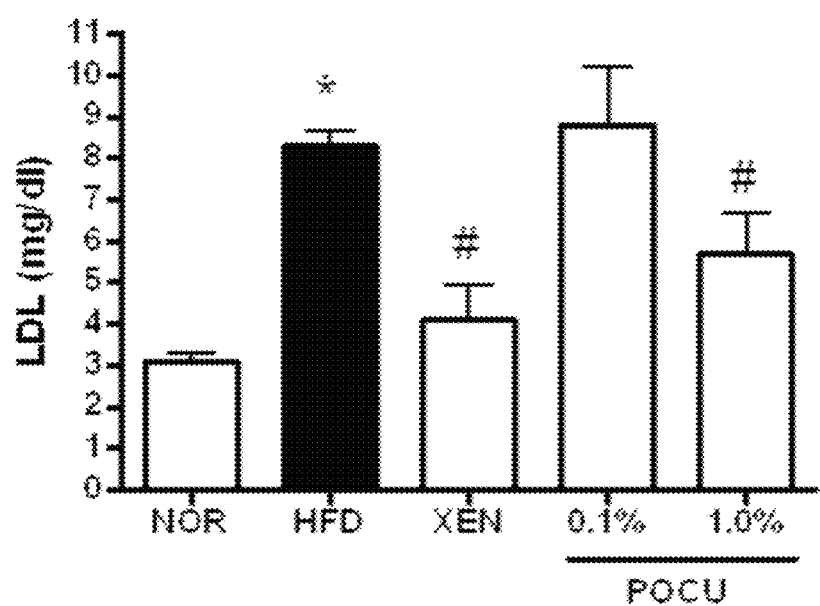

FIGS. 9 to 13 show changes in fats and lipids:

FIG. 9: total cholesterol;

FIG. 10: triglyceride;

FIG. 11: free fatty acids;

FIG. 12: high density lipoprotein (HDL);

FIG. 13: low density lipoprotein (LDL).

Figure 14:
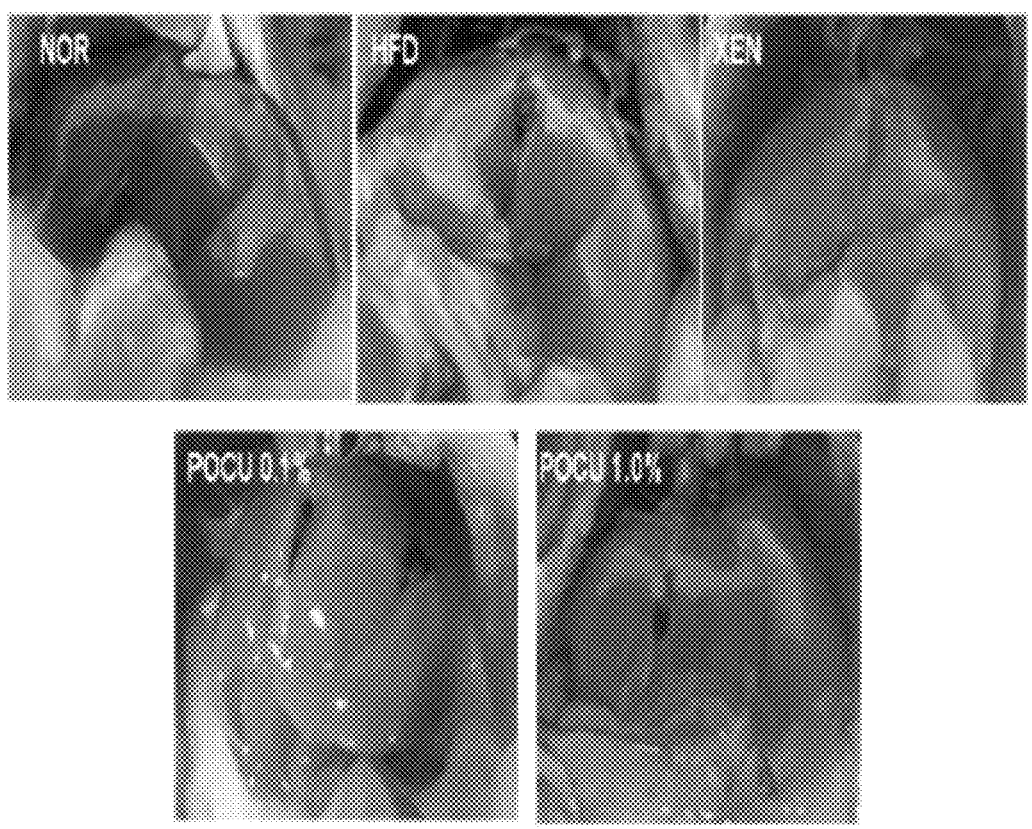

FIG. 14 shows the fatty liver-preventive effect in the *Polygonum cuspidatum* butanol fraction-administered group.

Figure 15:
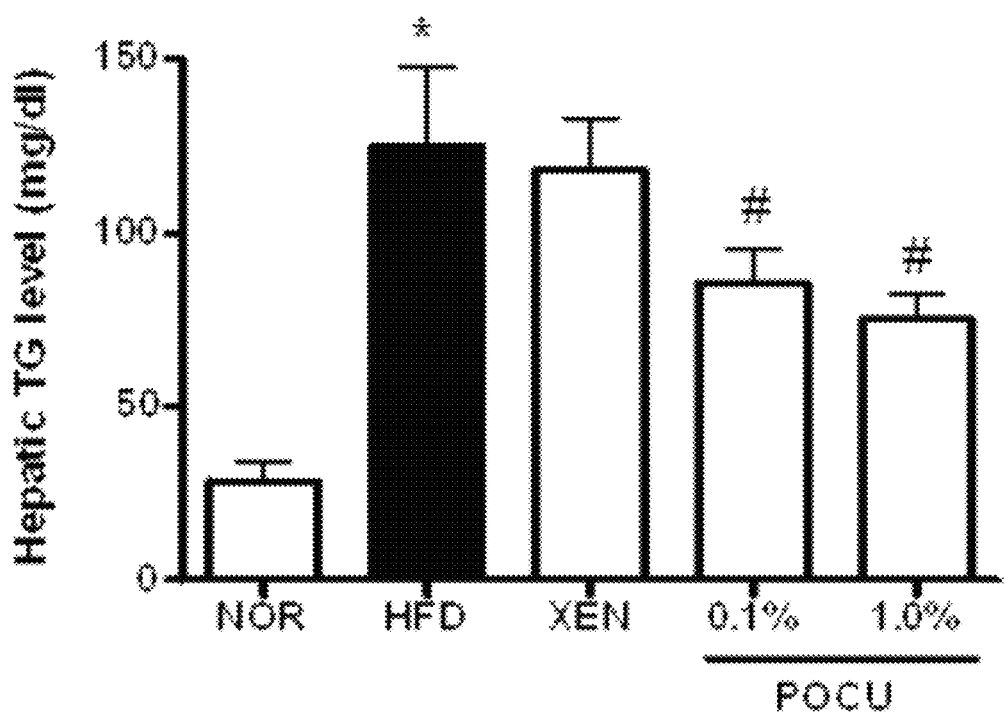

FIG. 15 shows the preventive effect on increases in amounts of triglycerides in the liver in the *Polygonum cuspidatum* butanol fraction-administered group.

Figure 16:
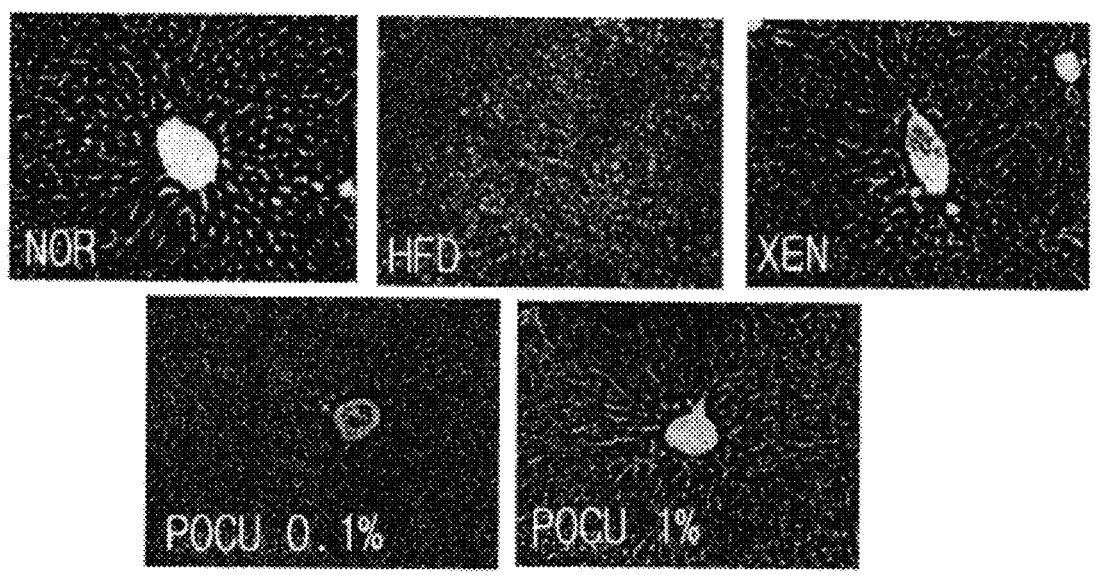

FIG. 16 shows the result of H&E staining regarding the fatty liver-preventive effect in the *Polygonum cuspidatum* butanol fraction-administered group.

Figure 17:
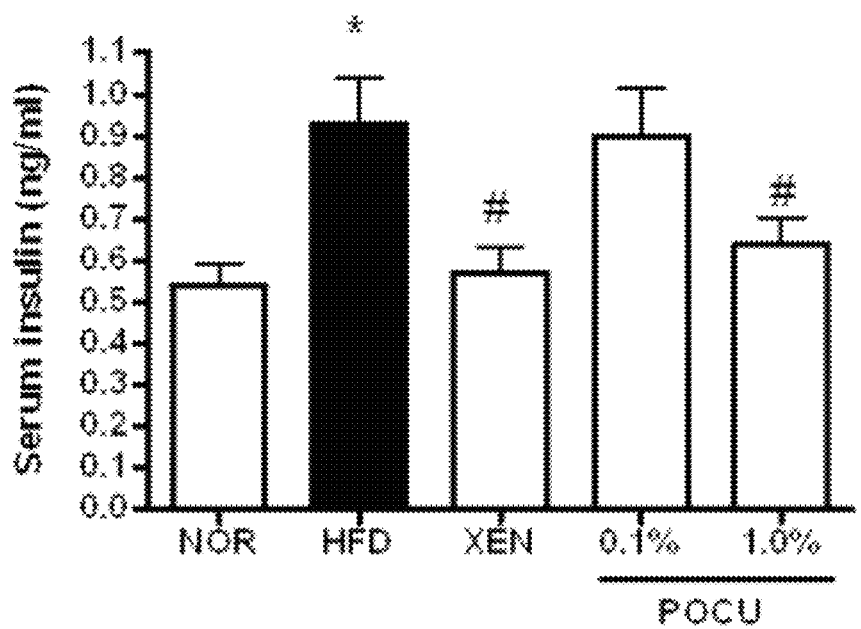

FIG. 17 shows the preventive effect on serum insulin resistance in the *Polygonum cuspidatum* butanol fraction-administered group.

Figure 18:
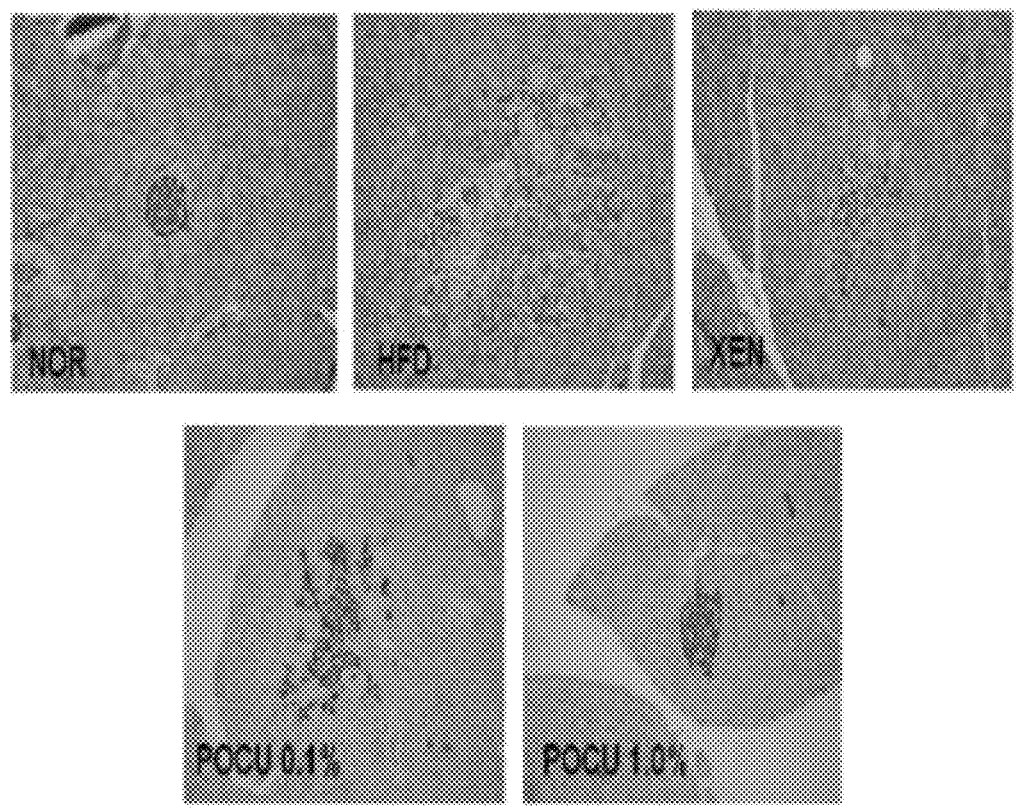

FIG. 18 shows the preventive effect on pancreatic beta cell disruption in the *Polygonum cuspidatum* butanol fraction-administered group.

Figure 19:
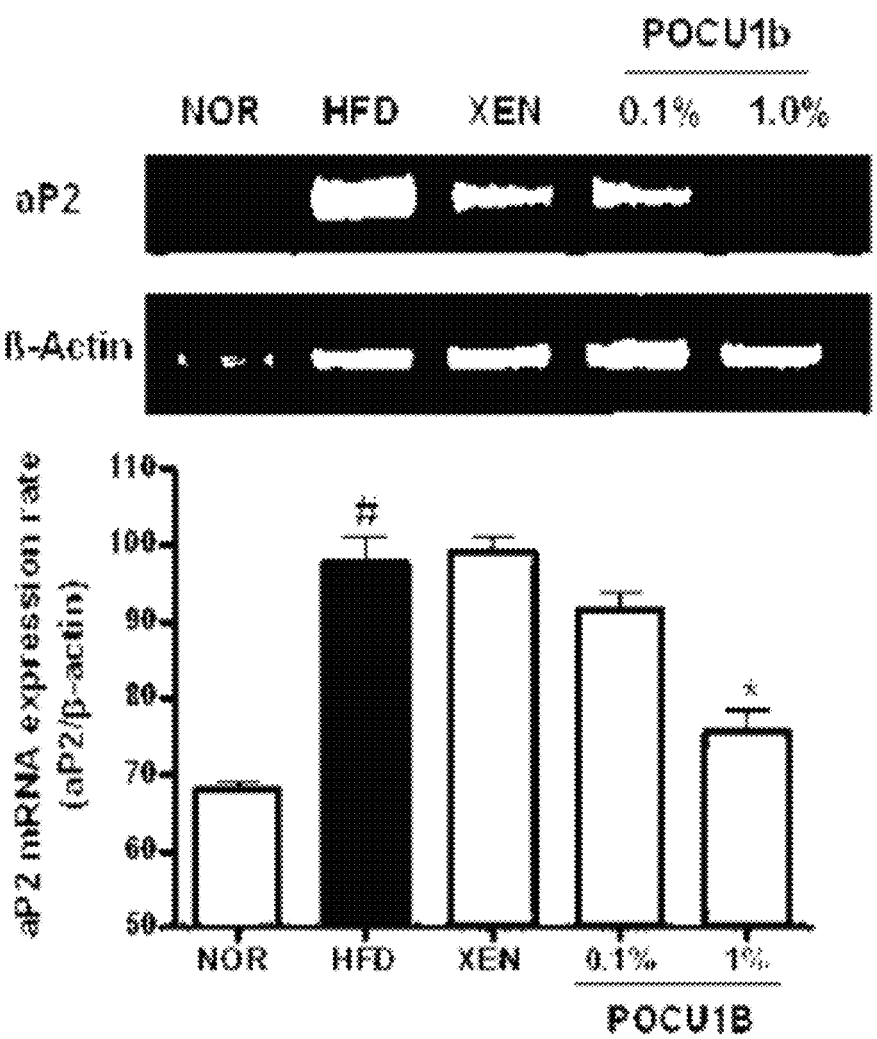

FIG. 19 shows the preventive effect on increases in the lipogenesis marker, aP2 mRNA in the *Polygonum cuspidatum* butanol fraction-administered group.

Figure 20:
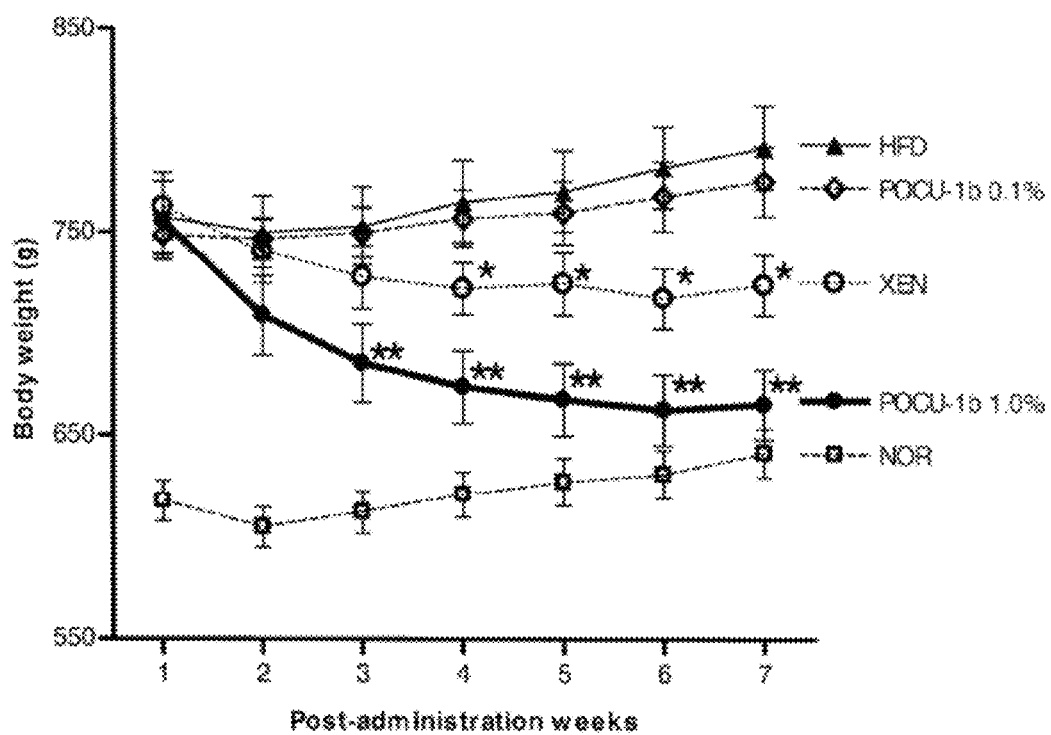

FIG. 20 shows the effect on body weight reduction in extremely obese rats, which is for the examination of the curative effect on obesity in the *Polygonum cuspidatum* butanol fraction-administered group.

Figure 21:
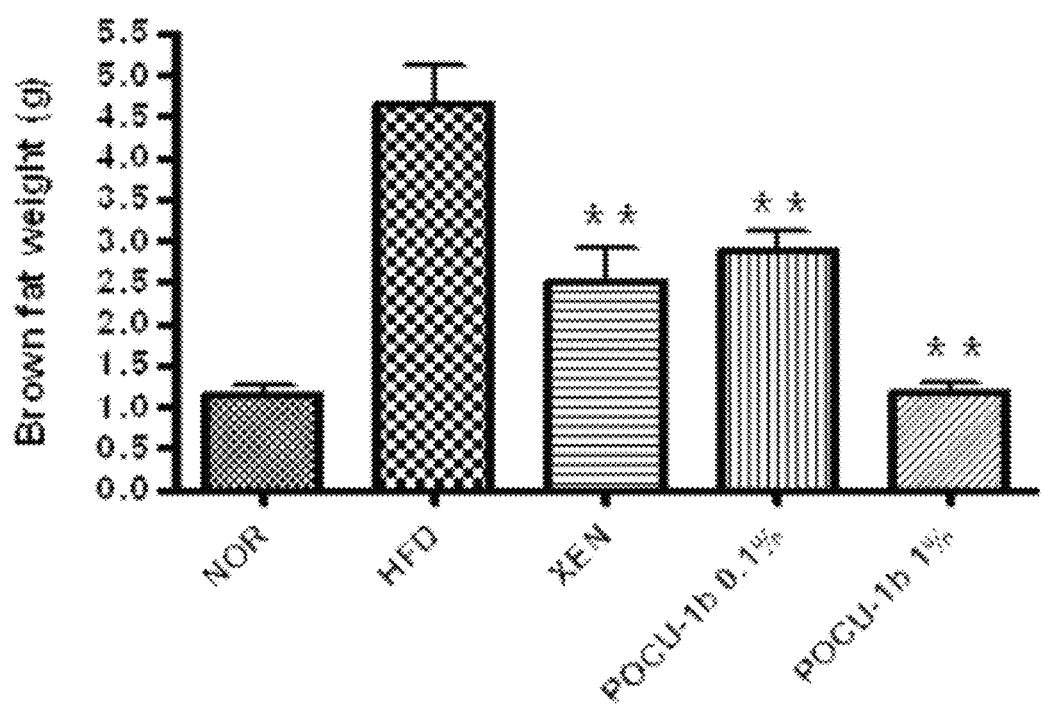
Figure 22:
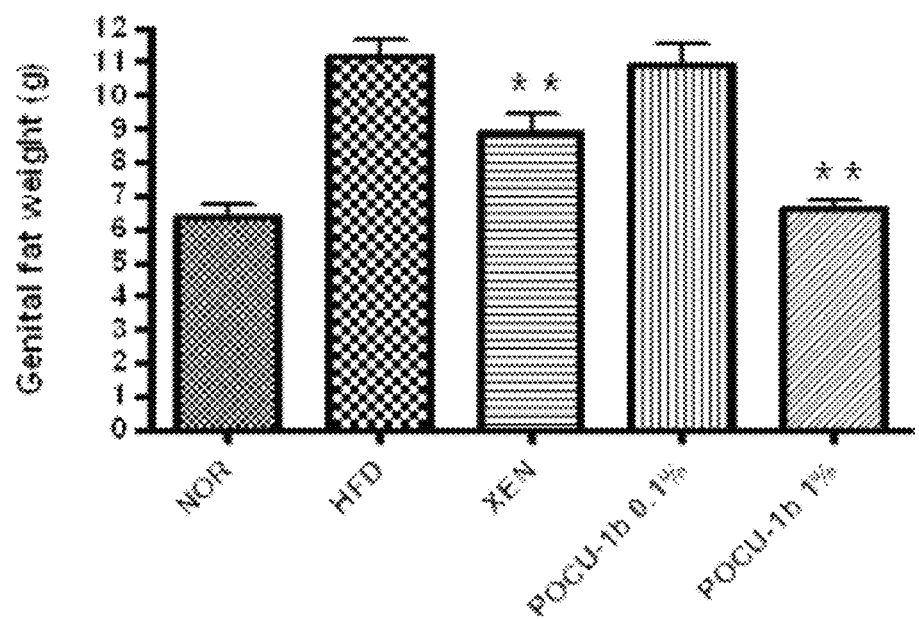
Figure 23:
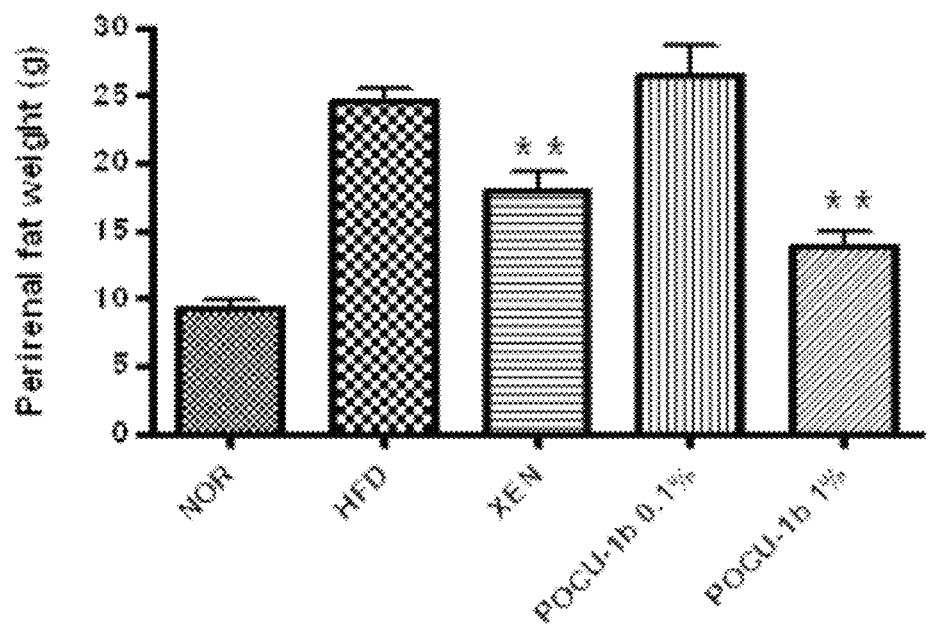
Figure 24:
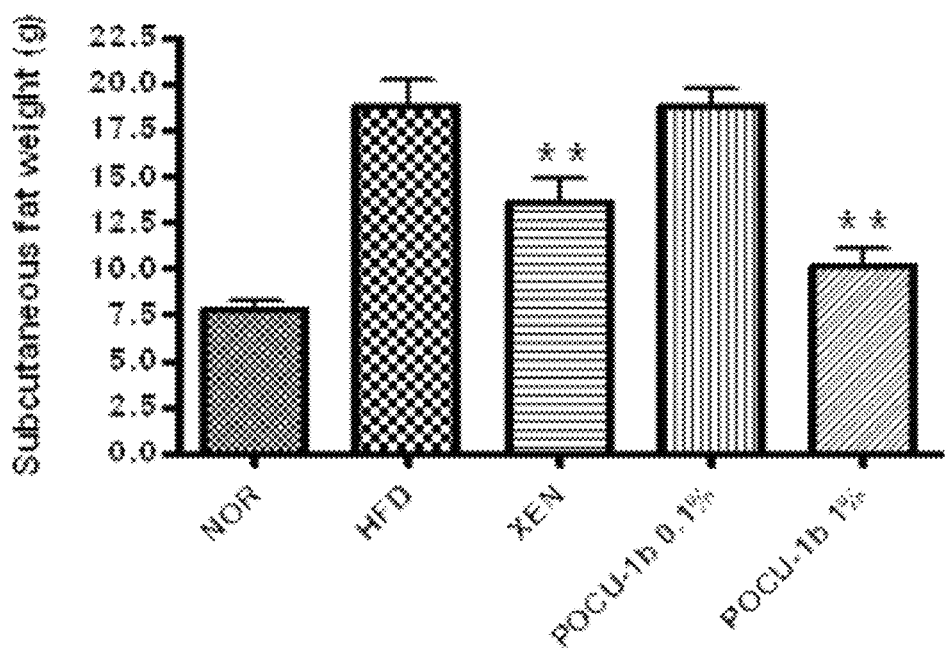

FIGS. 21 to 24 show the effect on fat weight reduction from each body part in extremely obese rats, which are for the examination of the curative effect on obesity in the *Polygonum cuspidatum* butanol fraction-administered group:

FIG. 21: brown fat;

FIG. 22: genital fat;

FIG. 23: perirenal fat;

FIG. 24: subcutaneous fat.

Figure 25:
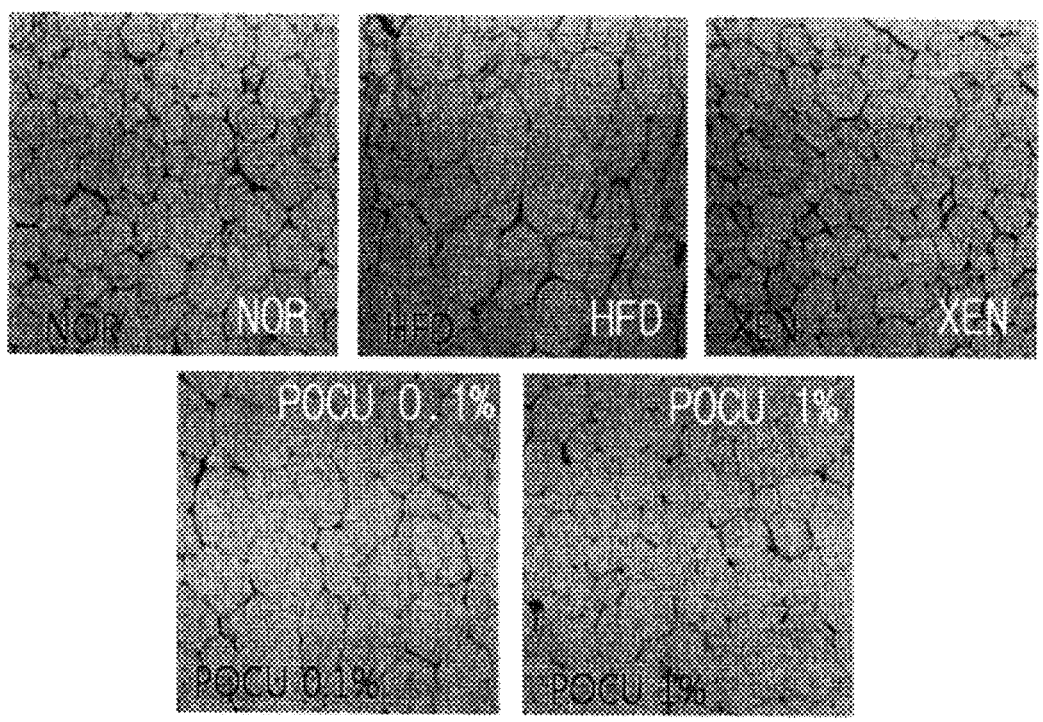
Figure 26:
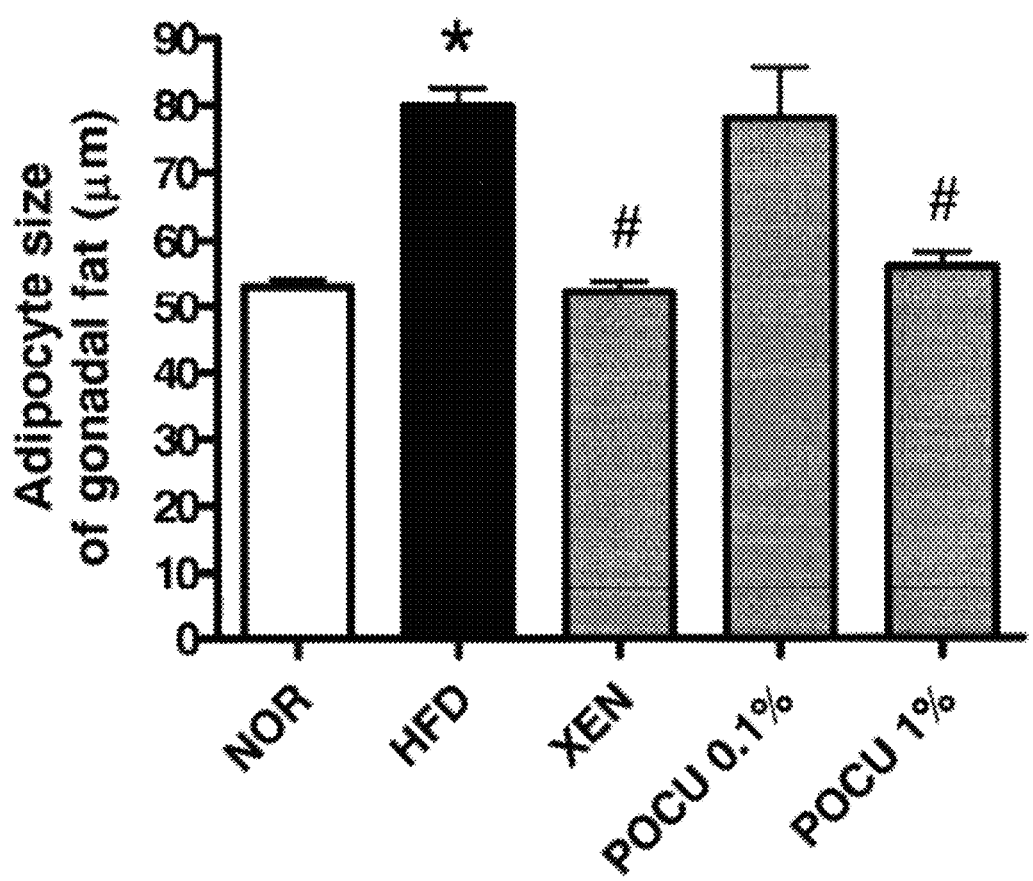

FIGS. 25 and 26 are photographs and a graph illustrating the effect of *Polygonum cuspidatum* butanol fraction on changes in adipocyte size.

Figure 27:
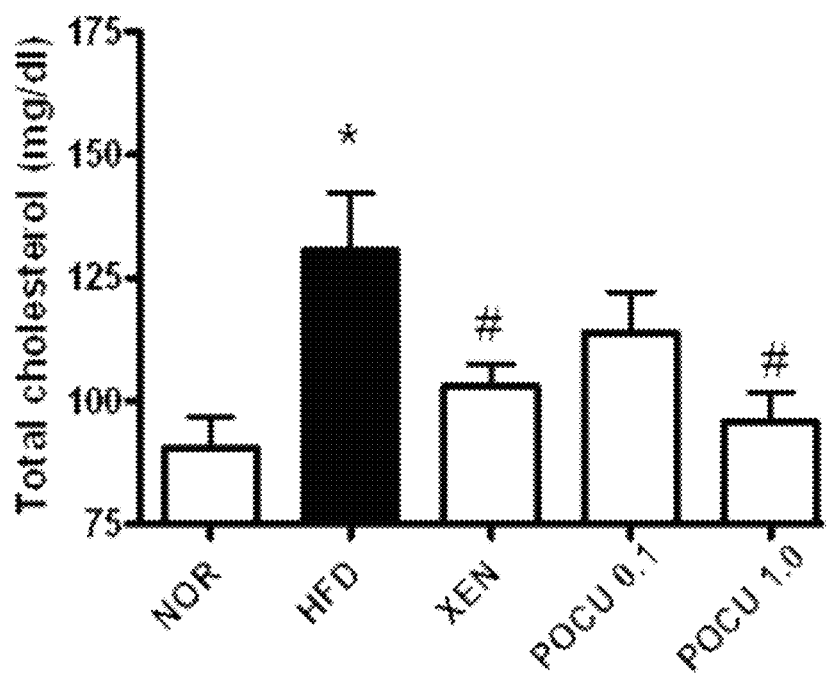
Figure 28:
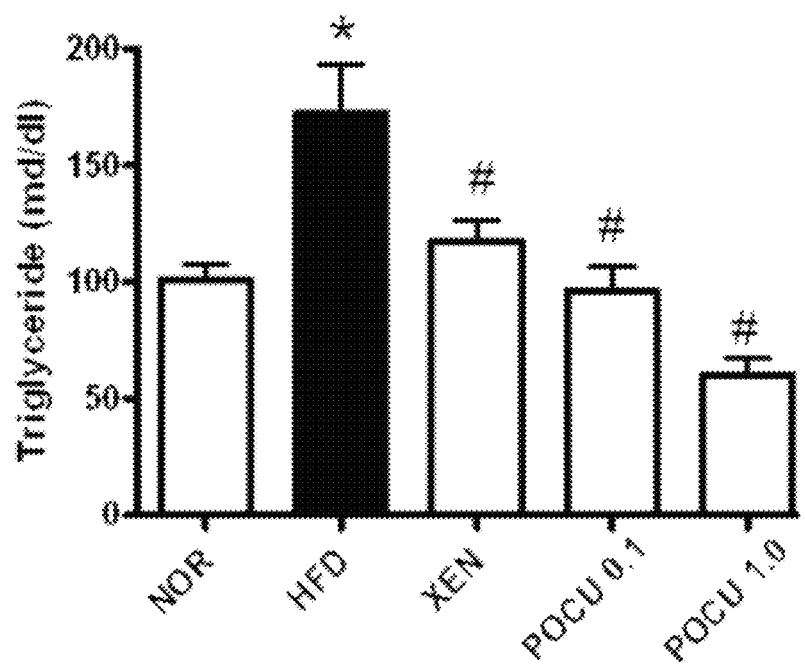
Figure 29:
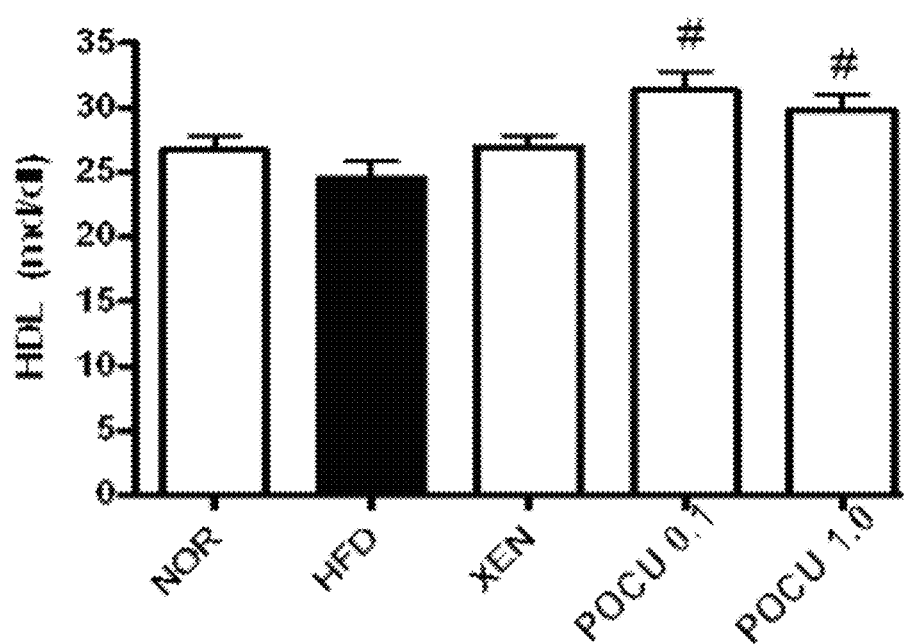
Figure 30:
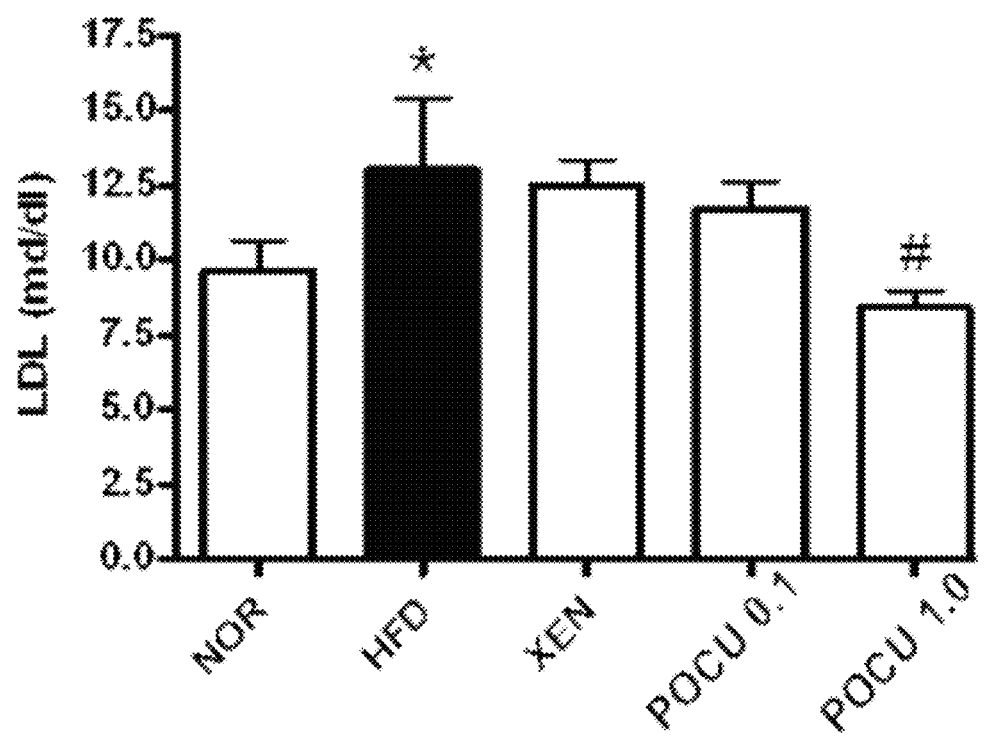

FIGS. 27 to 30 show changes in fats and lipids in the *Polygonum cuspidatum* butanol fraction-administered group:

FIG. 27: total cholesterol;

FIG. 28: triglyceride;

FIG. 29: HDL;

FIG. 30: LDL.

Figure 31:
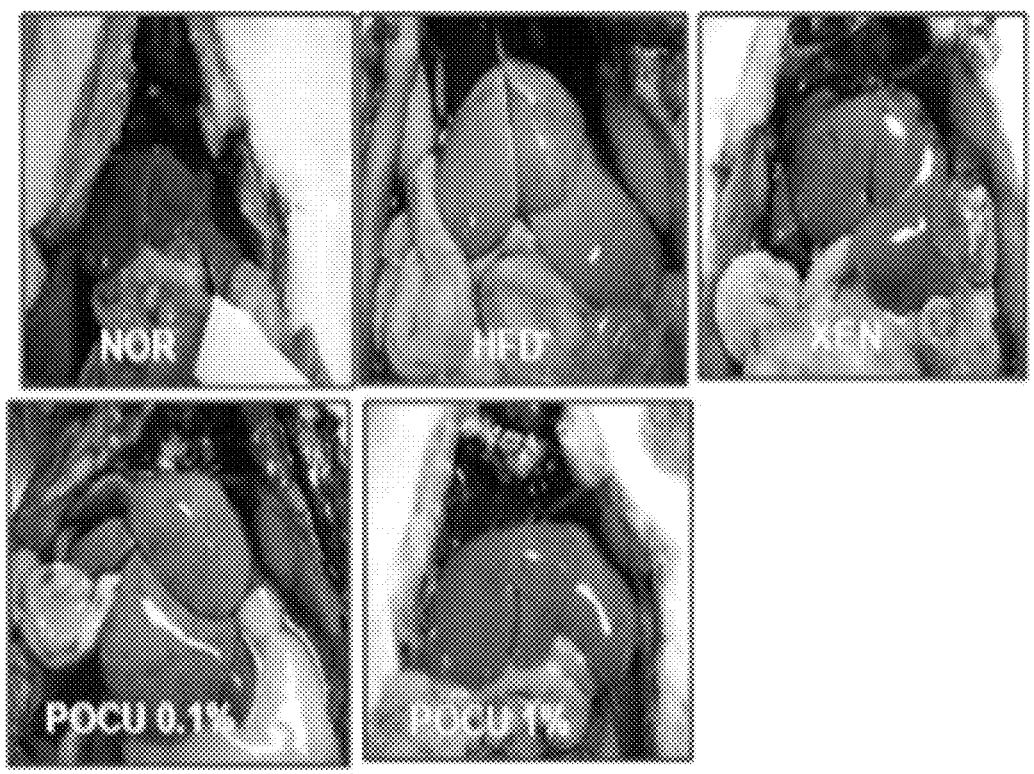

FIG. 31 shows the fatty liver-curative effect in the *Polygonum cuspidatum* butanol fraction-administered group.

Figure 32:
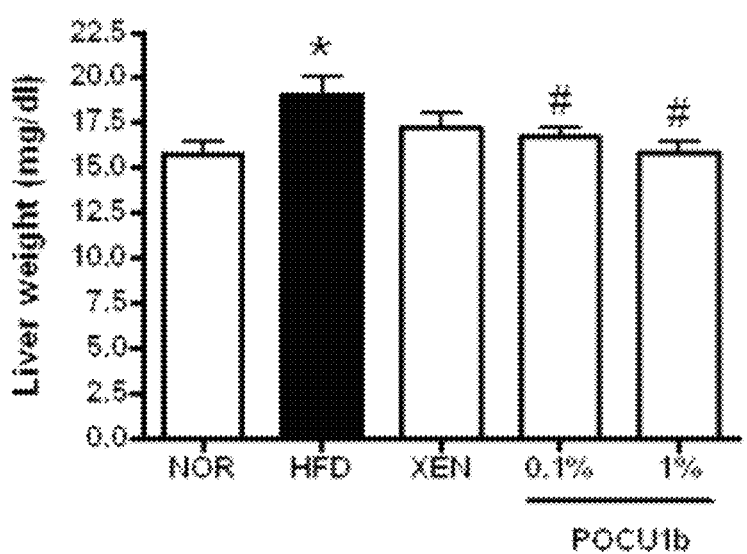

FIG. 32 shows changes in liver weight in the *Polygonum cuspidatum* butanol fraction-administered group.

Figure 33:
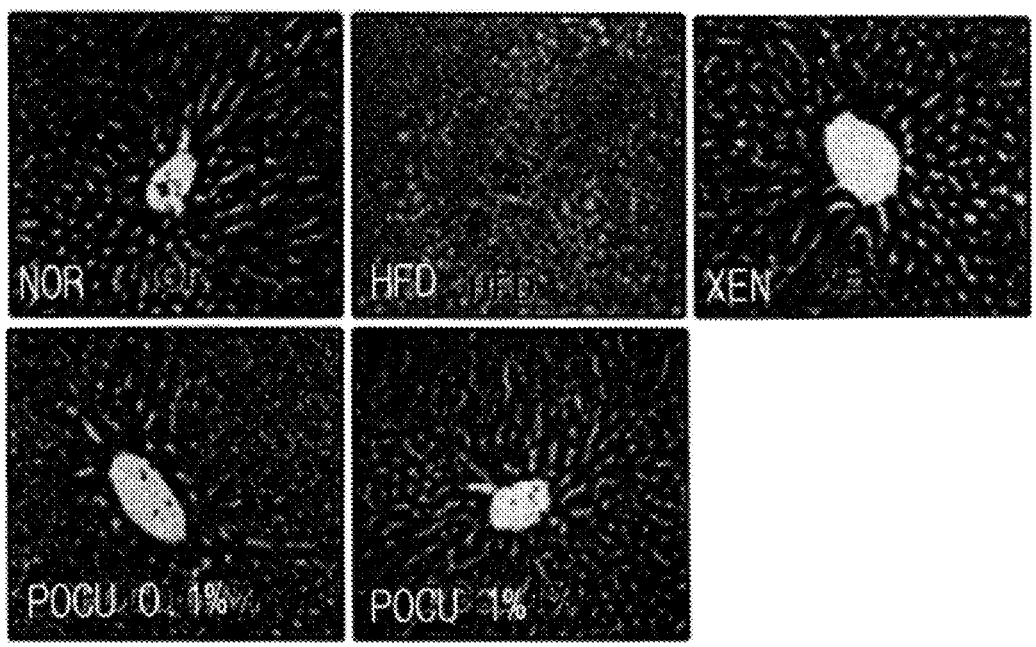

FIG. 33 shows the results of H&E staining of liver tissues in the *Polygonum cuspidatum* butanol fraction-administered group.

Figure 34:
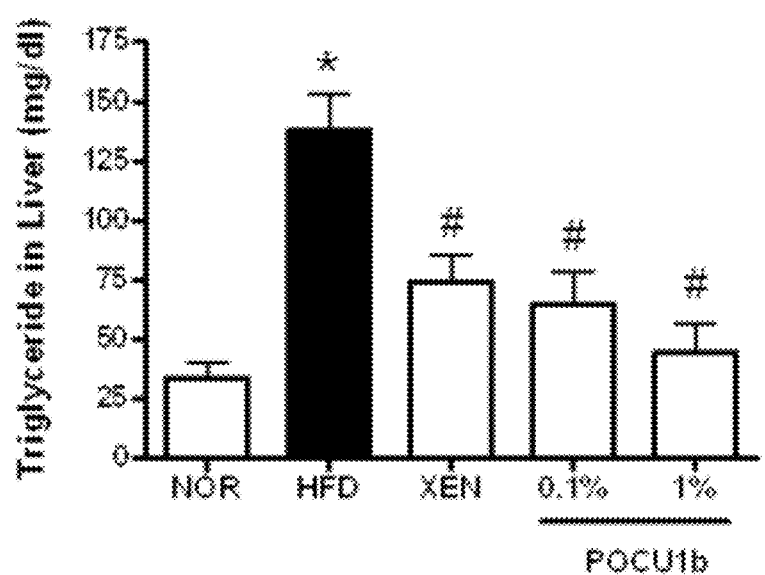

FIG. 34 shows the changes in amounts of triglycerides in liver in the *Polygonum cuspidatum* butanol fraction-administered group.

Figure 35:
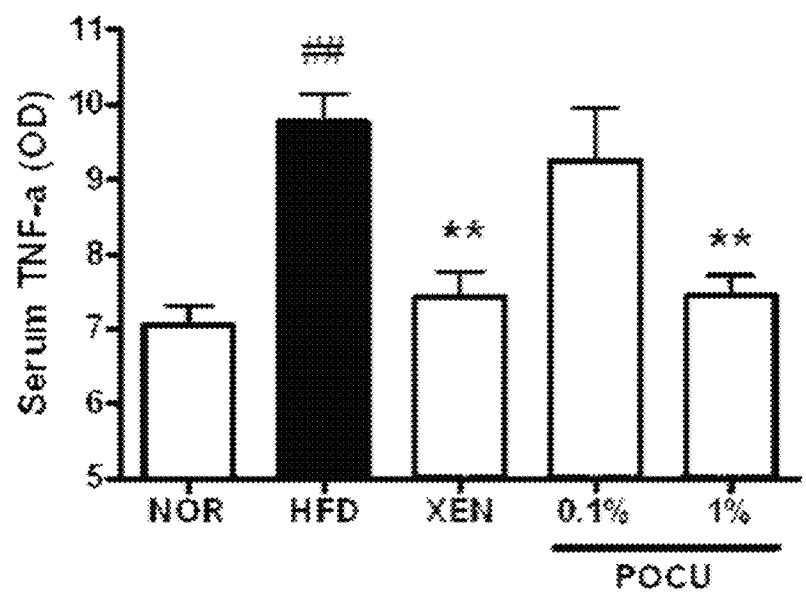
Figure 36:
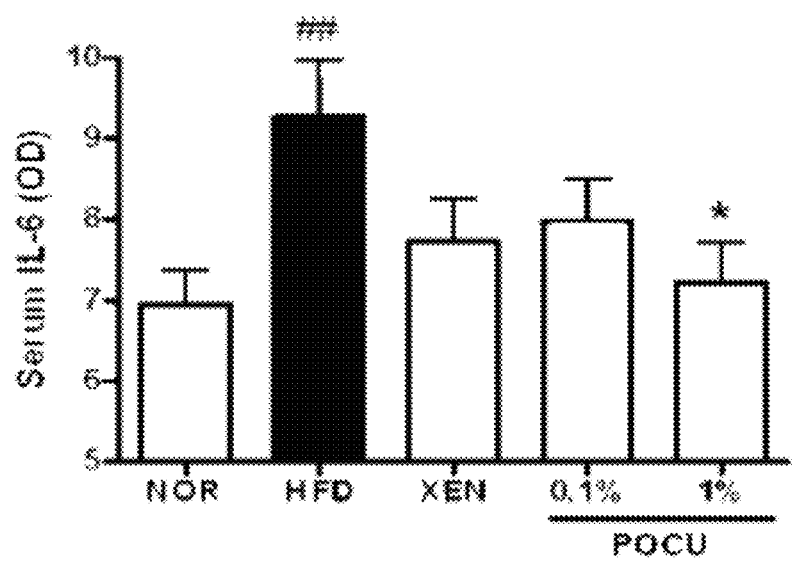

FIGS. 35 and 36 show the concentrations of serum IL-6 and serum TNF-α in the *Polygonum cuspidatum* butanol fraction-administered group.

Figure 37:
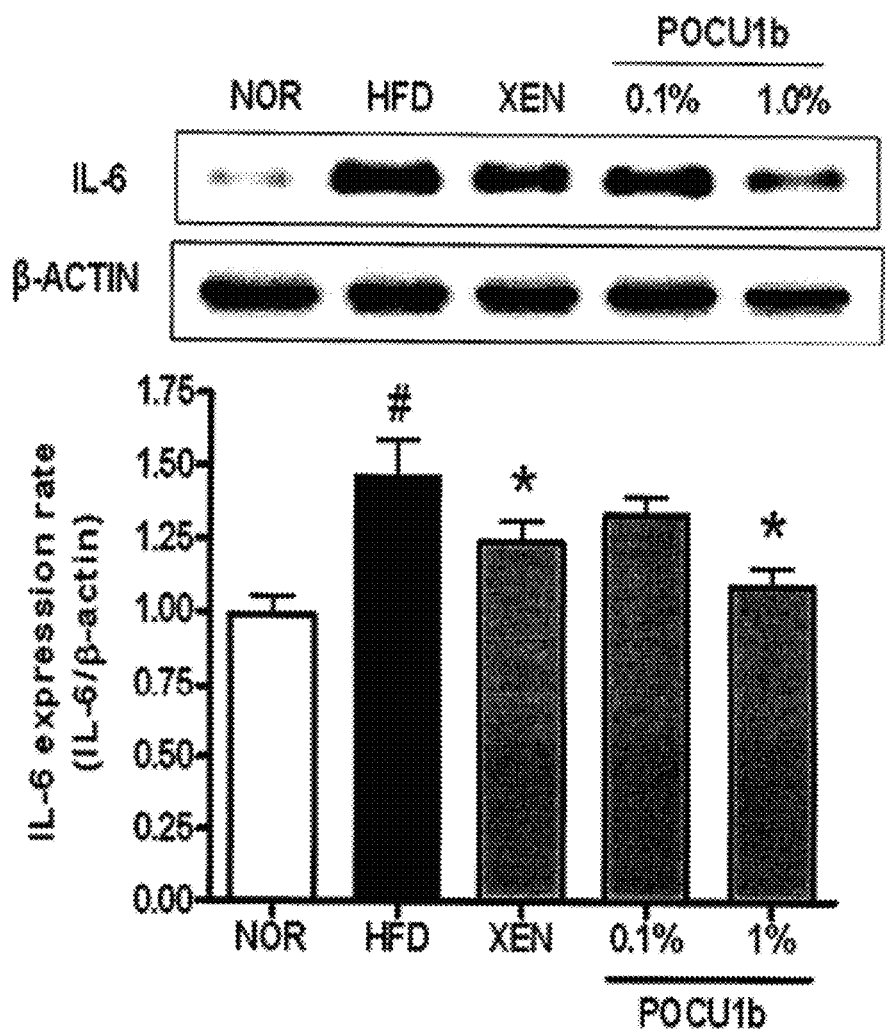
Figure 38:
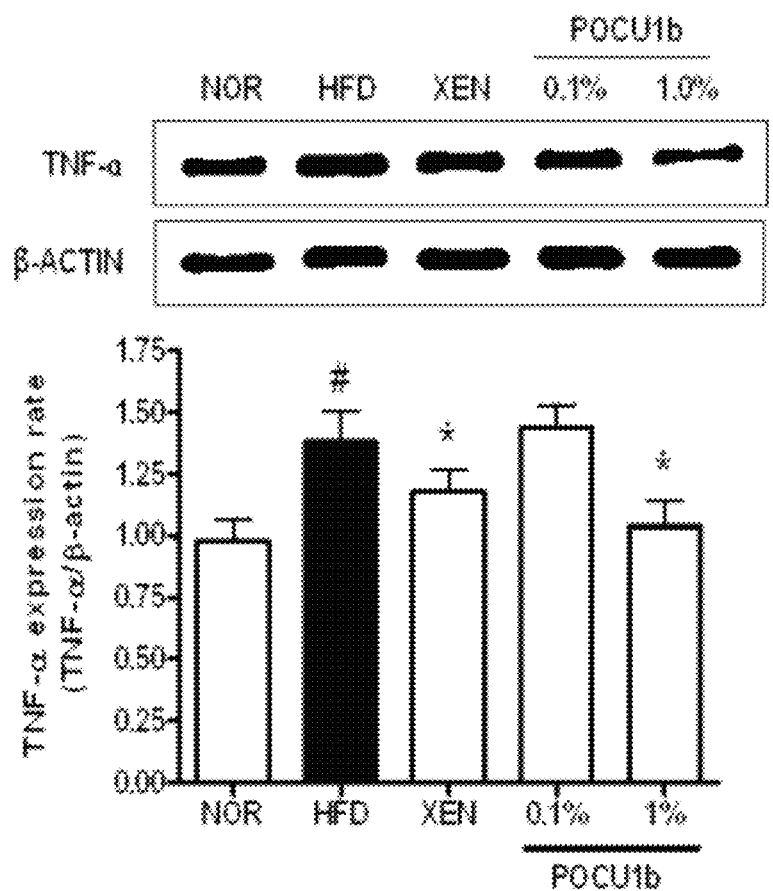
Figure 39:
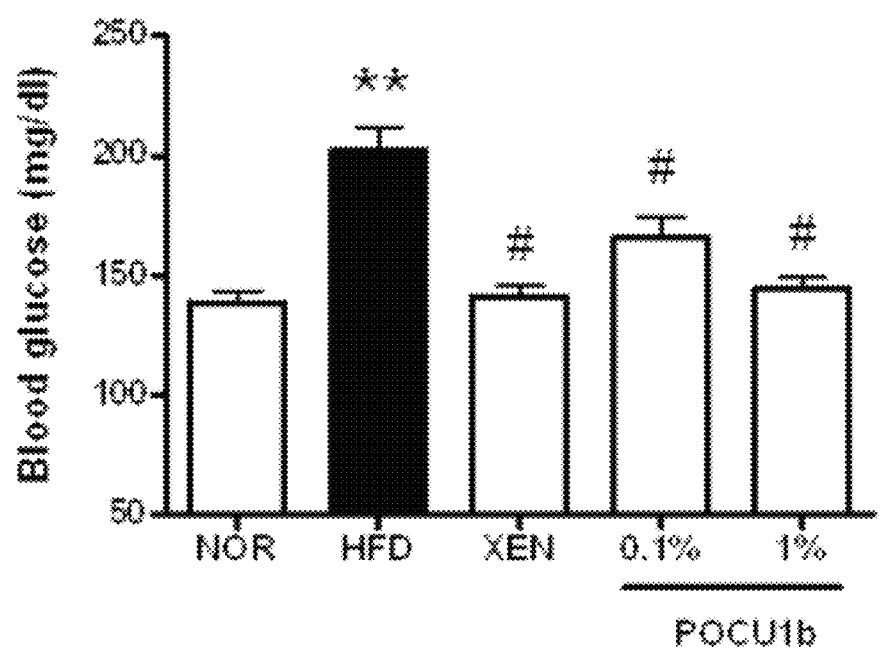
Figure 40:
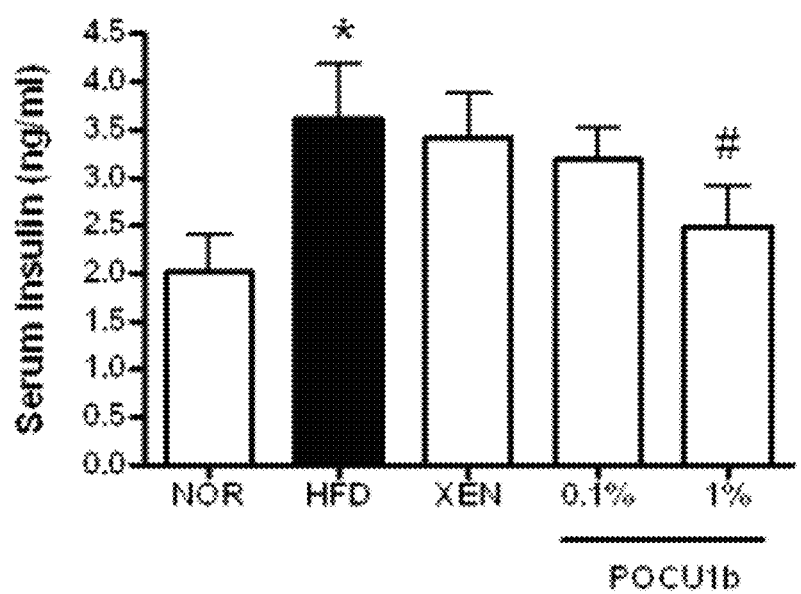
Figure 41:
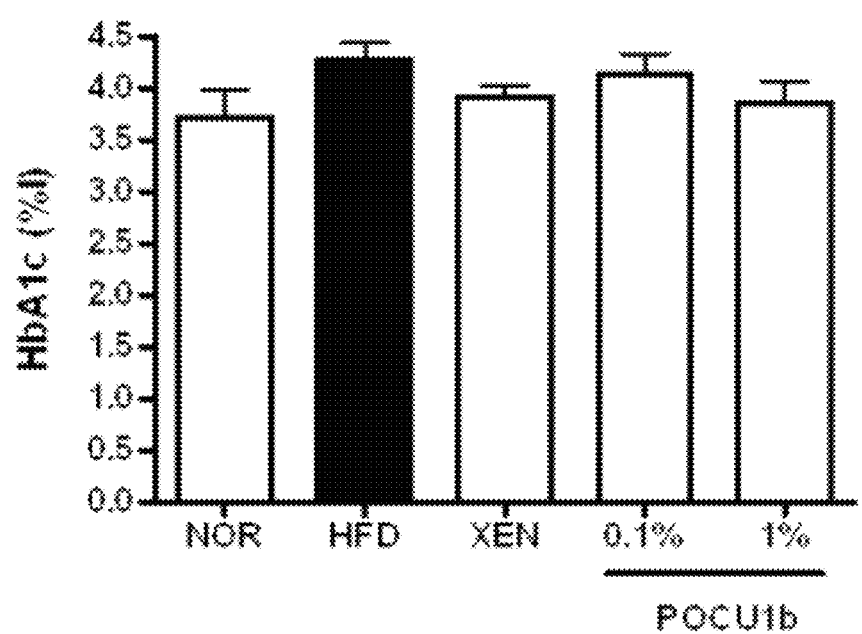
Figure 42:
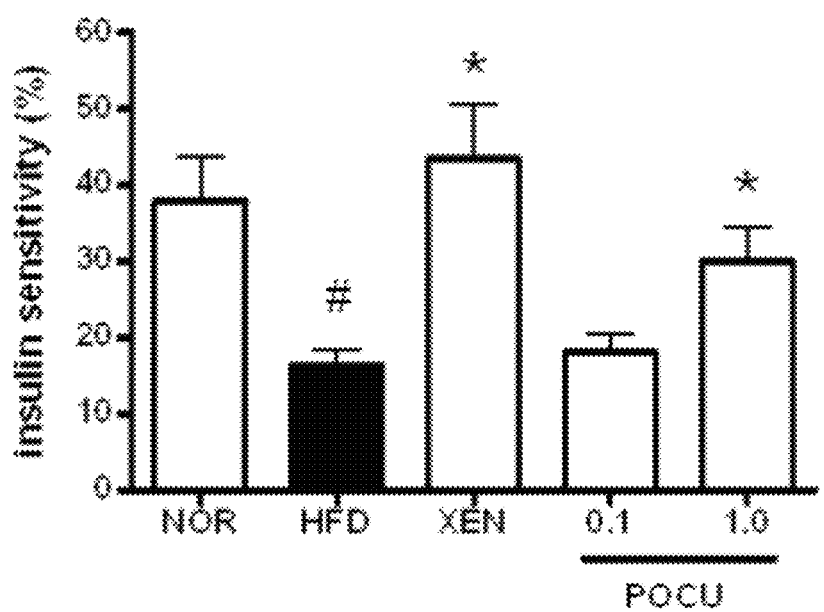
Figure 43:
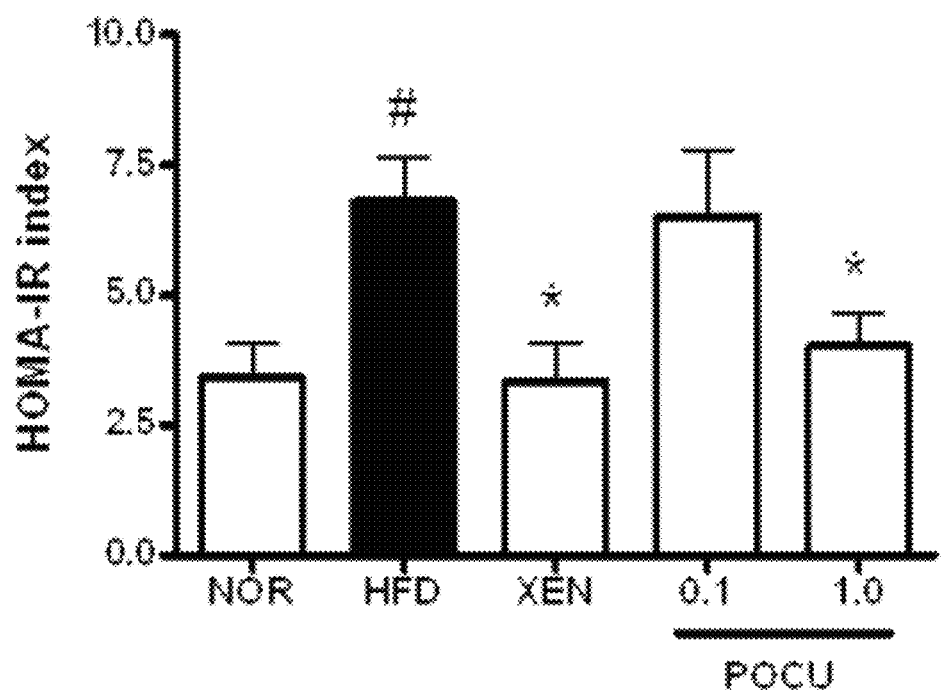

FIGS. 37 and 38 show the concentrations of IL-6 and TNF-α in adipose tissue in the *Polygonum cuspidatum* butanol fraction-administered group.

FIGS. 39 to 42 show the blood glucose, serum insulin, HbA1c, and insulin sensitivity in the *Polygonum cuspidatum* butanol fraction-administered group.

Figure 44:
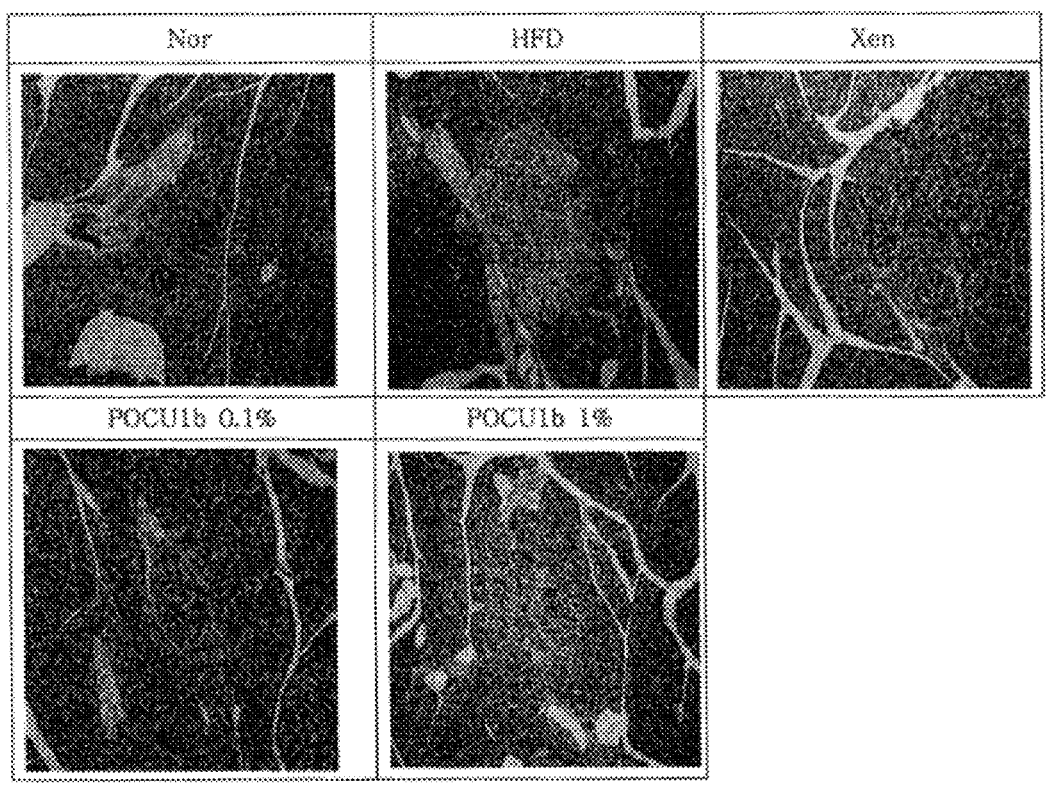

FIG. 44 shows the changes in pancreatic beta cells in the *Polygonum cuspidatum* butanol fraction-administered group.

Figure 45:
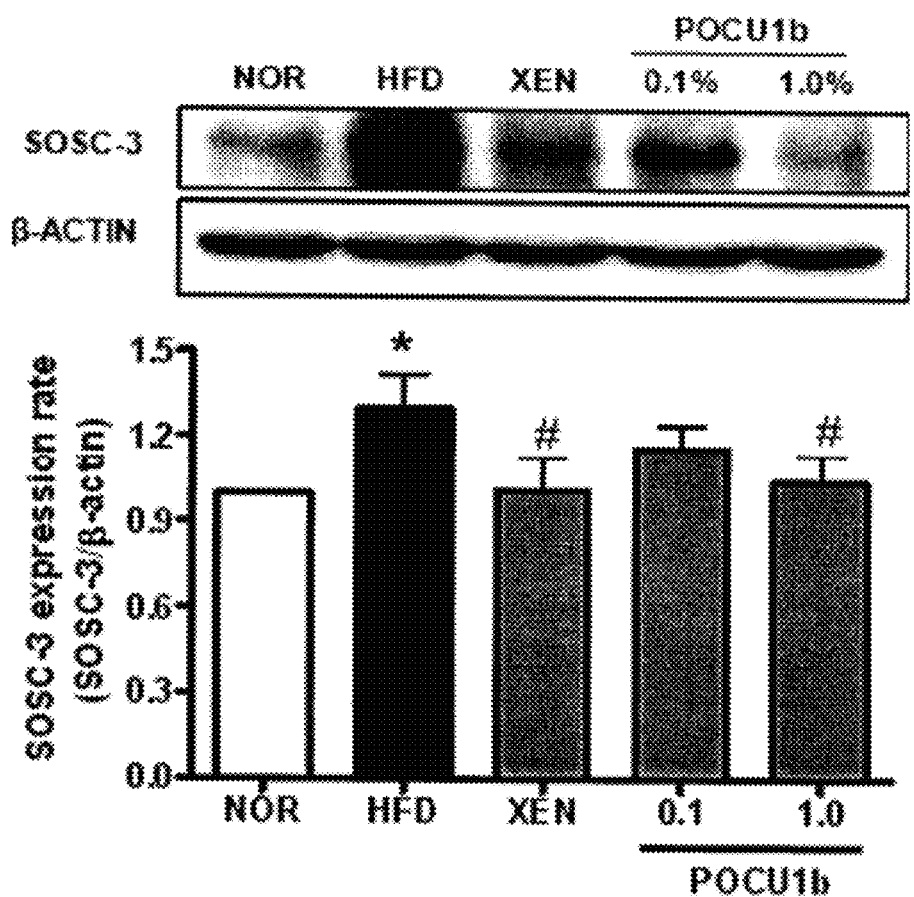

FIG. 45 shows Western blot analysis of SOCS proteins by a *Polygonum cuspidatum* butanol fraction treatment.

Figure 46:
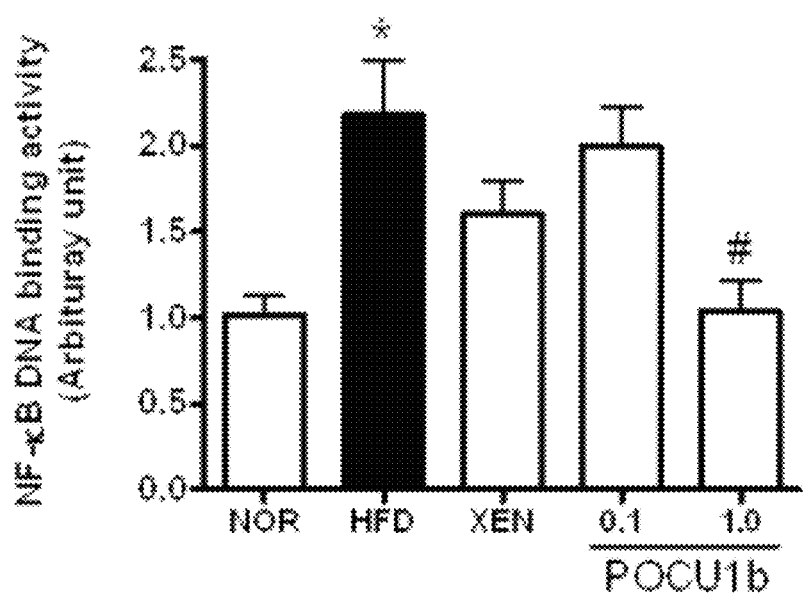

FIG. 46 shows the analysis of NF-κB DNA binding activity by a *Polygonum cuspidatum* butanol fraction treatment.

Figure 47:
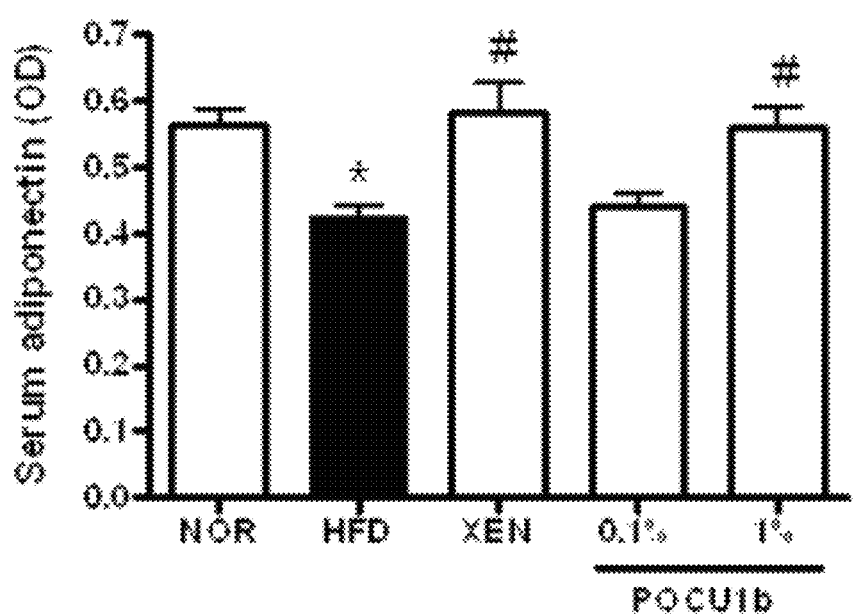

FIG. 47 shows the changes in the concentrations of serum adiponectin in the *Polygonum cuspidatum* butanol fraction-administered group.

Figure 48:
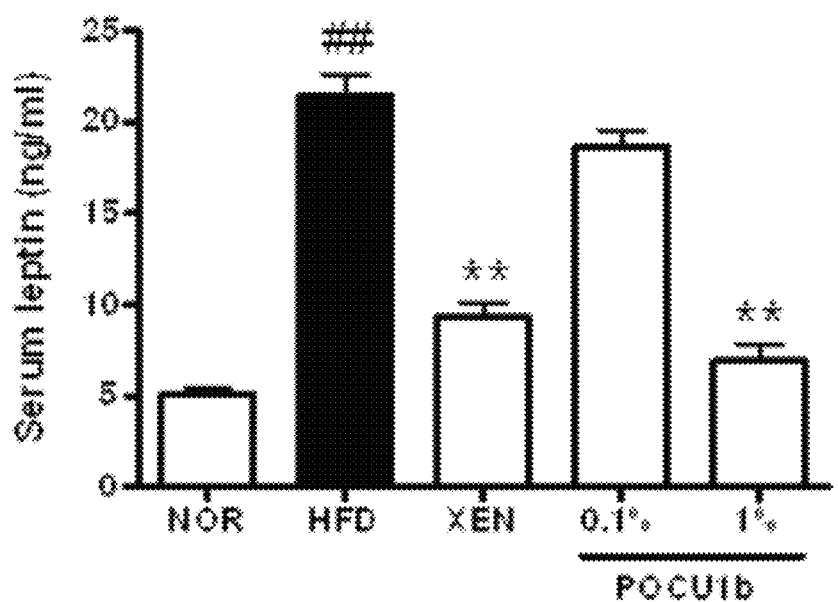

FIG. 48 shows the changes in the concentrations of serum leptin in the *Polygonum cuspidatum* butanol fraction-administered group.

Figure 49:
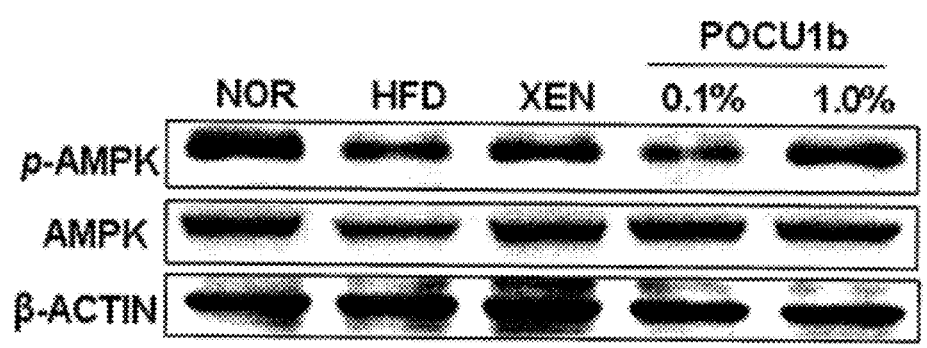
Figure 50:
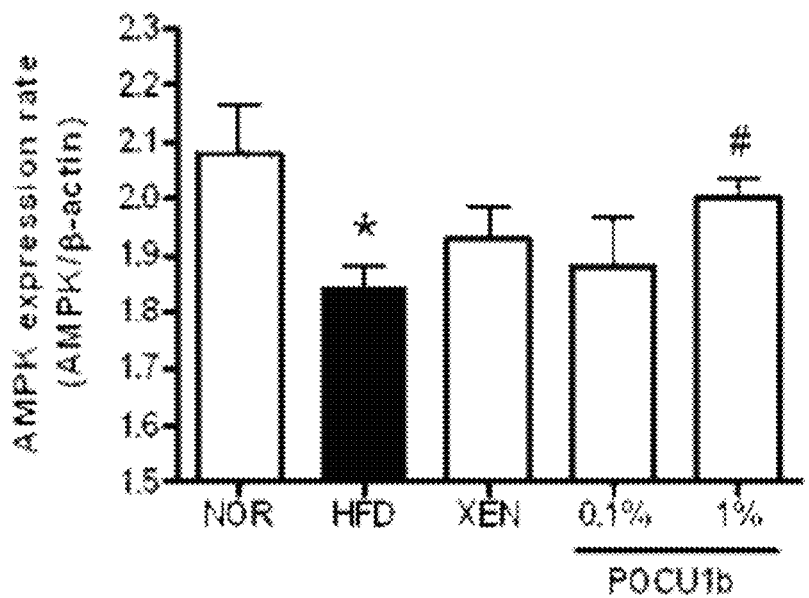
Figure 51:
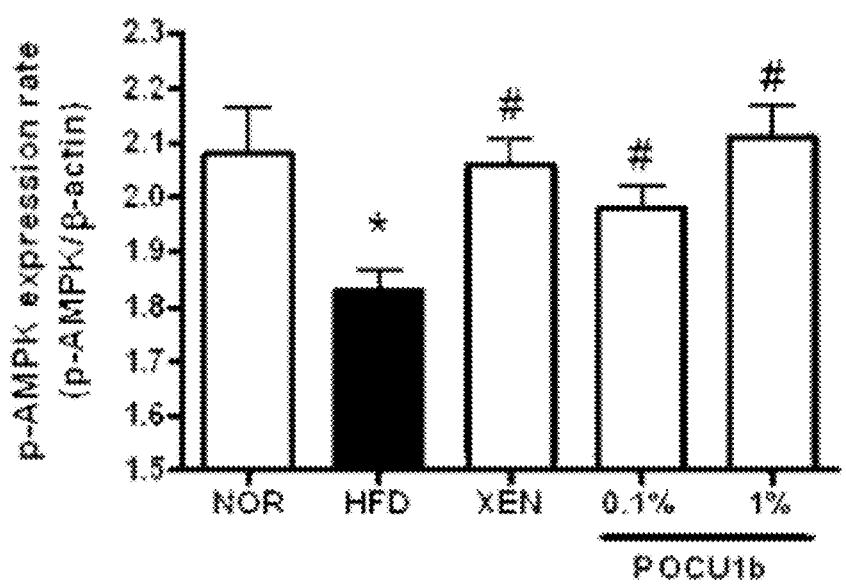

FIGS. 49 to 51 show the changes in AMPK protein expression in liver tissues in the *Polygonum cuspidatum* butanol fraction-administered group.

Figure 52:
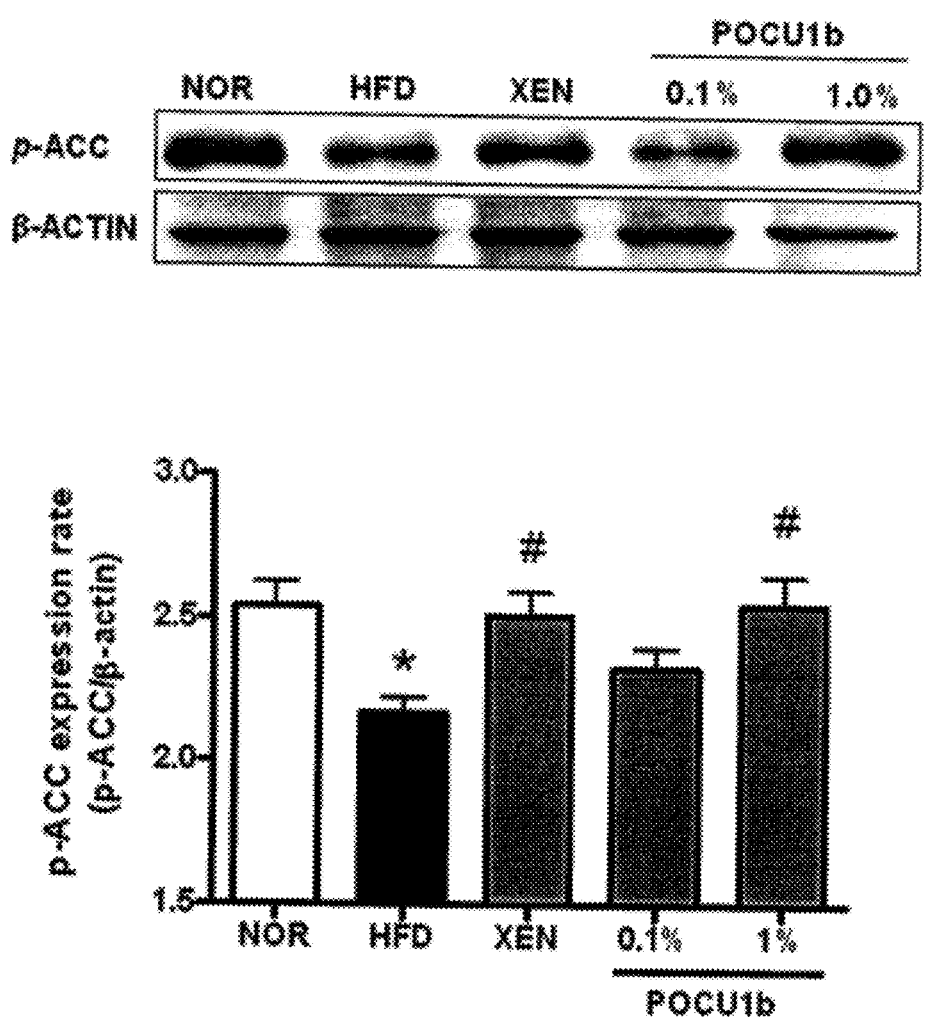

FIG. 52 shows the changes in ACC protein expression in liver tissues in the *Polygonum cuspidatum* butanol fraction-administered group.

Figure 53:
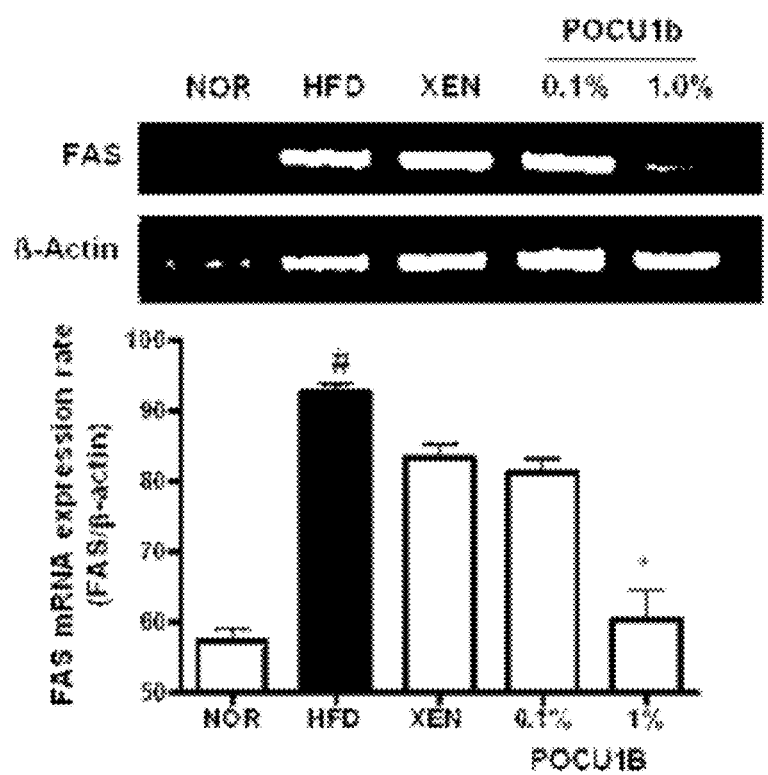

FIG. 53 shows the changes in FAS mRNA expression in liver tissues in the *Polygonum cuspidatum* butanol fraction-administered group.

Figure 54:
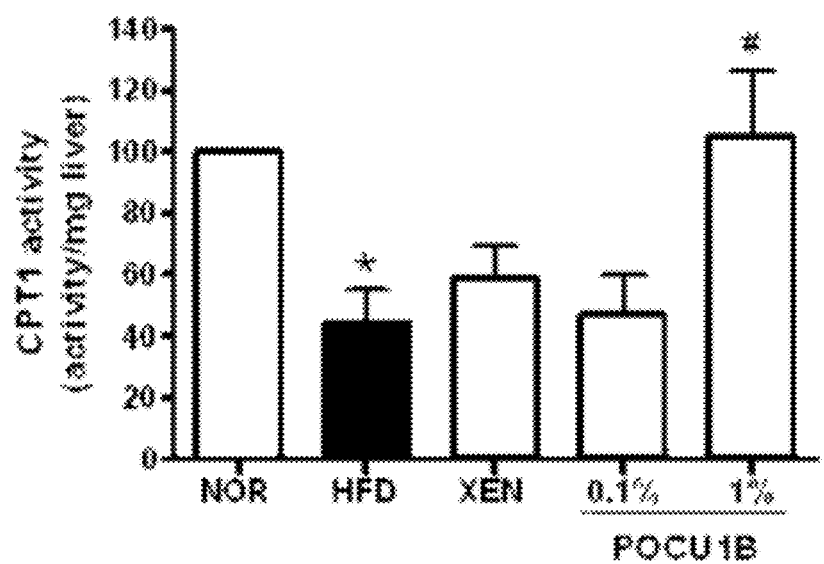

FIG. 54 shows the changes in CPT-1 activity in liver tissues in the *Polygonum cuspidatum* butanol fraction-administered group.

BEST MODE FOR CARRYING OUT THE INVENTION

In order to achieve the objects, the present invention provides a pharmaceutical composition for preventing and treating obesity comprising a fraction as an active ingredient, wherein the fraction is prepared by extracting *Polygonum cuspidatum* with water, an alcohol, or a mixed solvent thereof to obtain a *Polygonum cuspidatum* extract and further extracting the *Polygonum cuspidatum* extract with butanol.

The present invention also provides a functional food for preventing and relieving obesity, hyperlipidemia, and metabolic diseases comprising a fraction as an active ingredient, wherein the fraction is prepared by extracting *Polygonum cuspidatum* with water, an alcohol, or a mixed solvent thereof to obtain a *Polygonum cuspidatum* extract and further extracting the *Polygonum cuspidatum* extract with butanol.

Furthermore, the present invention provides a pharmaceutical composition for preventing and treating obesity comprising a fraction as an active ingredient, wherein the fraction is prepared by extracting *Polygonum cuspidatum* with water, an alcohol, or a mixed solvent thereof to obtain a *Polygonum cuspidatum* extract and further extracting the *Polygonum cuspidatum* extract with ethylacetate.

The present invention also provides a functional food for preventing and relieving obesity comprising a fraction as an active ingredient, wherein the fraction is prepared by extracting *Polygonum cuspidatum* with water, an alcohol, or a mixed solvent thereof to obtain a *Polygonum cuspidatum* extract and further extracting the *Polygonum cuspidatum* extract with ethylacetate.

Furthermore, the present invention provides a method of treating obesity, the method comprising administering a pharmaceutically effective amount of the *Polygonum cuspidatum* butanol fraction to an obese individual.

The present invention also provides a method of preventing obesity, the method comprising administering a pharmaceutically effective amount of the *Polygonum cuspidatum* butanol fraction to an obese individual.

Hereinafter, the present invention will be described in detail.

The present invention provides a pharmaceutical composition for preventing and treating obesity, hyperlipidemia, and metabolic diseases comprising a fraction as an active ingredient, wherein the fraction is prepared by extracting *Polygonum cuspidatum* with water, an alcohol, or a mixed solvent thereof to obtain a *Polygonum cuspidatum* extract and further extracting the *Polygonum cuspidatum* extract with butanol or ethylacetate.

The present inventors studied *Polygonum cuspidatum*, extracts, *Polygonum cuspidatum* fractions, and a monocompound extracted therefrom, resveratrol, and confirmed that the curative effect on obesity of the butanol fraction and the ethylacetate fraction of *Polygonum cuspidatum* is remarkably higher than that of a *Polygonum cuspidatum* water extract, an *Polygonum cuspidatum* ethanol extract, and resveratrol, and thereby, the present inventors found out that the fractions of *Polygonum cuspidatum* can be used for treating and preventing obesity.

The extract of *Polygonum cuspidatum* may be prepared by general extraction methods known in the art, such as ultrasonic extraction, filtration, and reflux extraction.

The extract of *Polygonum cuspidatum* may be extracted with water, C1 to C4 lower alcohol, or a mixed solvent thereof, and preferably methanol or ethanol.

The solvent may be used in an amount of 1 to 10 times, preferably 1 to 5 times, the volume of *Polygonum cuspidatum*.

A hexane fraction in the present invention was obtained by adding water and hexane into a residue, which is obtained by evaporating the solvent from the extract, and separating a hexane layer. An ethylacetate fraction in the present invention was also obtained by mixing ethylacetate into the water layer, where the hexane layer was eliminated; and separating an ethylacetate layer. Furthermore, a butanol fraction in the present invention was also obtained by removing the ethylacetate layer; mixing butanol into a layer where the ethylacetate layer was eliminated; and separating a butanol layer. Finally, a water layer was obtained after removing the butanol layer (Examples 1 to 6).

Among the extracts, the water extract and the ethanol extract, and among the fractions, the hexane fraction, the ethylacetate fraction, and the butanol fraction, and a purified and separated compound, resveratrol, were used to examine the inhibitory effect on pancreatic lipase, a target of a therapeutic agent for obesity (Experimental example 1 and Table 1). As a result, the butanol fraction was 4.6, 22, 7.8 times more effective than the ethanol extract, the water extract, and resveratrol, respectively. The ethylacetate fraction was 2.7, 13.4, 4.7 times more effective than the ethanol extract, the water extract, and resveratrol, respectively in inhibiting pancreatic lipase.

In order to examine the inhibitory effect on absorption of lipid emulsions, in vivo experiment was carried out (Experimental example 2 and Table 2). The butanol fraction of the *Polygonum cuspidatum* ethanol extract had excellent effect next only to Xenical, a positive control. The inhibitory effect of the ethylacetate fraction on absorption of lipid emulsions was also remarkably more effective than those of the water extract, the ethanol extract, and resveratrol.

Thus, the present inventors found that the butanol fraction and the ethylacetate fraction of the *Polygonum cuspidatum* extract inhibit absorption of fat in a living body and can be used for a pharmaceutical composition for treating and preventing obesity.

After confirmation that the butanol fraction and the ethylacetate fraction of the *Polygonum cuspidatum* extract inhibit pancreatic lipase activity and absorption of lipid emulsions, the obesity-preventive effect was evaluated through a real animal experiment.

Figure 2:
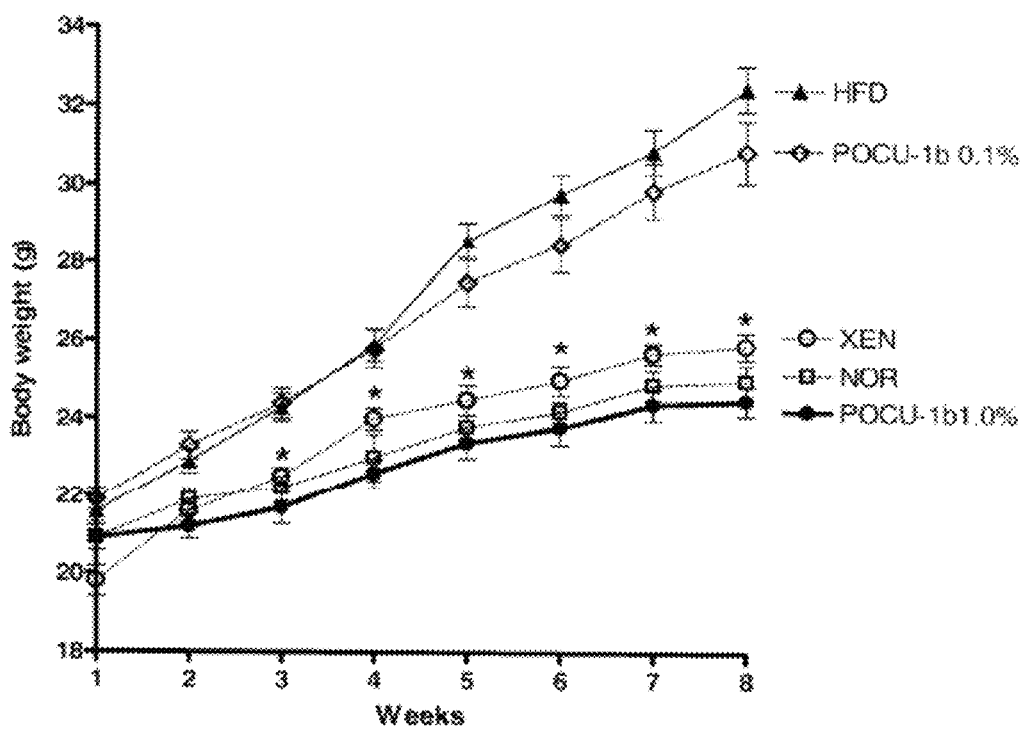
FIG. 2 shows the preventive effect of a *Polygonum cuspidatum* butanol fraction on obesity.

In order to examine the obesity-preventive effect, the present inventors observed the inhibitory effect on lipogenesis in animals (Experimental example 3). When 1% of the butanol fraction of the *Polygonum cuspidatum* extract was administered, changes in the body weight were very similar to those of the normal group and the inhibitory effect on lipogenesis in animals is more excellent than that of the commercially available Xenical (FIGS. 2 and 3).

As a result from observing the effect on increase in fats from each body part, increase rate in fats was low in all the subcutaneous fat, gonadal fat, and perirenal fat (FIGS. 4 to 6).

In order to examine those changes in body weight at a cellular level, fat tissues were removed and observed. The adipocyte size was remarkably reduced in the *Polygonum cuspidatum* butanol fraction-administered group (FIGS. 7 and 8).

Fatty livers were collected from rats received a high-fat diet and the butanol fraction and fat accumulation (Experimental, examples 3 and 4 and FIG. 14), changes in the amount of triglycerides in the liver (FIG. 15), changes in liver tissues through H&E staining of liver tissues (FIG. 16), changes in the amount of serum insulin (FIG. 17), changes in pancreatic beta cells (FIG. 18), and changes in the lipogenesis marker aP2 expression (FIG. 19) were examined. Fat accumulation in the liver was inhibited, the amount of triglycerides was reduced, changes in liver tissues were small, changes in the amount of serum insulin were small, the disruption in pancreatic beta cells was inhibited, and the expression of the adipogenic marker was inhibited. Thus, it was found that the butanol fraction of the *Polygonum cuspidatum* extract has the preventive effect on obesity.

Through a real animal test, the obesity-curative effect was evaluated.

In order to examine the obesity-curative effect, the body weight reduction was examined in high-fat diet-induced obese rats. As shown in Experimental example 4, it was found that the butanol fraction has the reductive effect on body weight (FIG. 20). As a result of examining reduction in fats from each body part, when 1% of the *Polygonum cuspidatum* butanol fraction was administered, the reductive effect was remarkable in all the brown fat, genital fat, perirenal fat, and subcutaneous fat (FIGS. 21 to 24). The adipocyte size was also maintained within the normal range (FIG. 25). From these results, it was found that the butanol fraction of the *Polygonum cuspidatum* extract has the remarkable obesity-curative effect.

Fatty livers were collected from high-fat diet-induced obese rats and obese rats but administered with the butanol fraction of the *Polygonum cuspidatum* extract. Fat accumulation (Experimental examples 4 and 5 and FIG. 31), changes in liver weight (FIG. 32), changes in liver tissues through H&E staining of liver tissues (FIG. 33), changes in the amount of triglycerides in the liver (FIG. 34), concentrations of IL-6 and TNF-α in blood and fat tissues (FIGS. 35 and 36), changes in blood glucose, serum insulin, HbA1c, insulin sensitivity (FIGS. 39 to 43), and changes in pancreatic beta cells (FIG. 44) were examined. Fats in liver were removed, liver weights were reduced, the amount of triglycerides was reduced, the concentrations of IL-6 and TNF-α in blood and fat tissues were reduced, all the blood glucose, serum insulin, HbA1c, and insulin sensitivity were similar to the normal group. Thus, it was found that the butanol fraction of the *Polygonum cuspidatum* extract has the obesity-curative effect.

The present invention provides a pharmaceutical composition for preventing and treating hyperlipidemia comprising a fraction as an effective ingredient, wherein the fraction is prepared by extracting *Polygonum cuspidatum* with water, an alcohol, or a mixed solvent thereof to obtain a *Polygonum cuspidatum* extract, and further extracting the *Polygonum cuspidatum* extract with butanol or ethylacetate.

In order to prove the hyperlipidemia-preventive effect, bloods were collected from rats received high-fat diet along with the butanol fraction of the *Polygonum cuspidatum* extract and increases in total cholesterol, triglycerides, free fatty acids, HDL, and LDL, which are fat metabolism-related markers, were examined. Even in the high-fat diet group, fat metabolism-related markers in the butanol fraction of the *Polygonum cuspidatum* extract-administered group were remarkably reduced and thus, the effect on hyperlipidemia was confirmed (Experimental examples 3 and 5 and FIGS. 9 to 13).

In order to prove the hyperlipidemia-curative effect, bloods were collected from obesity-induced rats and rats which were obesity-induced but the butanol fraction of the *Polygonum cuspidatum* extract was administered and increases in fat metabolism-related markers such as total cholesterol, triglycerides, free fatty acids, HDL, and LDL, were examined. Even in the high-fat diet group, fat metabolism-related markers in the butanol fraction of the *Polygonum cuspidatum* extract-administered group were remarkably reduced, and thus, the effect on hyperlipidemia was confirmed (Experimental example 4-4' and FIGS. 27 to 30).

The present invention provides a pharmaceutical composition for preventing and treating metabolic diseases comprising a fraction as an effective ingredient, wherein the fraction is prepared by extracting *Polygonum cuspidatum* with water, an alcohol, or a mixed solvent thereof to obtain a *Polygonum cuspidatum* extract, and further extracting the *Polygonum cuspidatum* extract with butanol or ethylacetate.

The present inventors observed the effect of the butanol fraction of the *Polygonum cuspidatum* extract on fat metabolism (Experimental examples 4 to 7) and found that the concentrations of serum adiponectin and serum leptin, which are factors affecting fat metabolism, were reduced to be within the normal range.

In order to investigate the effect of the butanol fraction on lipid metabolism, changes in AMPK protein expression in liver tissues, ACC protein expression in liver tissues, FAS mRNA expression in liver tissues, and CPT-1 activity in liver tissues were observed and the results in the butanol fraction-administered group were similar to those in the normal group (FIGS. 47 to 54). From these results, it was found that the butanol fraction of the *Polygonum Cuspidatum* extract is effective in maintaining fat metabolism and can be used for a pharmaceutical composition for preventing and treating lipid-metabolic diseases.

The present invention may contain 0.1 to 99.9 weight % of the fraction of the *Polygonum Cuspidatum* extract of the present invention with respect to the total weight of the pharmaceutical composition and may comprise pharmaceutically acceptable carriers, excipients, or diluents.

The pharmaceutical composition of the present invention may have various oral or parenteral formulations. Generally used diluents, such as fillers, extenders, binders, wetting agents, disintegrants and surfactants, or excipients are used for pharmaceutical preparations. Solid formulations for oral administration include tablets, pills, powders, granules, capsules, etc. These solid formulations are prepared by mixing one or more compounds with at least one or more excipients, such as starch, calcium carbonate, sucrose or lactose, gelatin, etc. Also, in addition to simple excipients, lubricants such as magnesium stearate, talc, etc. may be used. Liquid formulations for oral administration include suspensions, liquid for internal use, emulsions, syrups, etc. In addition to generally-used simple diluents such as water and liquid paraffin, various excipients such as wetting agents, sweeteners, aromatics, preservatives, etc. may be included. Formulations for parenteral administration include sterile solutions, non-aqueous solutions, suspensions, emulsions, freeze-dried preparations, and suppository. Propylene glycol, polyethylene glycol, vegetable oil such as olive oil, injectable ester such as ethyloleate, etc. may be used for the non-aqueous solutions and suspensions. Witepsol, macrogol, Tween 61, cocoa butter, laurin butter, glycerogelatin, etc. may be used for a suppository base.

Individuals for which the pharmaceutical composition of the present invention can be applicable may be vertebrates, preferably mammals, more preferably experimental animals such as rats, mice, rabbits, guinea pigs, hamsters, dogs, and cats, and most preferably anthropoids such as chimpanzees, gorillas, and humans.

The pharmaceutical composition of the present invention may be administered orally or parenterally. For parenteral administration, skin external use or intraperitoneal injection, intrarectal injection, intravenous injection, intramuscular injection, subcutaneous injection, epidural injection in uterine, or intracerebrovascular injection may be selected, and most preferably, the pharmaceutical composition of the present invention may be used for skin external use.

The administration dose of the composition of the present invention may be different depending on body weight, age, gender, health condition of patient, diet, time of administration, method of administration, excretion rate, and severity of diseases to be treated and the daily administration dose may be from about 0.01 to about 1000 mg/kg of the fraction of *Polygonum cuspidatum* extract, preferably from about 30 to about 500 mg/kg, more preferably from about 50 to about 300 mg/kg and the administration frequency may be once to six times a day.

The pharmaceutical composition of the present invention may be used alone or in combination with surgery, radiation therapy, hormonal, therapy, chemical therapy, and methods using biological regulators.

The present invention also provides a functional food for preventing and relieving one or more diseases selected from the group consisting of obesity, hyperlipidemia, and metabolic diseases comprising a fraction as an effective ingredient, wherein the fraction is prepared by extracting *Polygonum cuspidatum* with water, an alcohol, or a mixed solvent thereof to obtain a *Polygonum cuspidatum* extract, and further extracting the *Polygonum cuspidatum* extract with butanol or ethylacetate.

Since *Polygonum cuspidatum* is a natural extract being already used for a drug and has no biotoxicity and is considered to be safe, it can be used for a health food. In addition, the butanol fraction or the ethylacetate fraction of the *Polygonum cuspidatum* extract has excellent obesity-preventive and curative effect and it can be used for a functional food for preventing and relieving obesity.

The functional food of the present invention may further comprise various flavoring agents or natural carbohydrates. The natural carbohydrates include monosaccharides such as glucose and fructose, disaccharides such as maltose and sucrose, polysaccharides such as dextrin and cyclodextrin, and sugar alcohols such as xylitol, sorbitol, and erythritol. Sweeteners include natural sweeteners such as thaumatin and stevia extracts, and synthetic sweeteners such as saccharin and aspartame. The natural carbohydrates may be used in an amount of from about 0.01 to about 0.04 parts by weight, and preferably from about 0.02 to about 0.03 parts by weight per 100 parts by weight of the health food of the present invention.

In addition, the functional food of the present invention may comprise various nutraceuticals, vitamins, electrolytes, flavoring agents, colorants, pectic acid or its salt, alginic acid or its salt, organic acids, protective colloidal thickeners, pH adjusters, stabilizers, preservatives, glycerin, alcohol, carbonating agents used in carbonated drinks, etc. Also, the functional food of the present invention may comprise fruit flesh for preparation of natural fruit juices, fruit juice beverages and vegetable juices. These components may be used alone or in combination. Although not critical, these additives are generally used in an amount of from about 0.01 to 0.1 parts by weight per 100 parts by weight of the health food of the present invention.

Furthermore, the present invention provides a method of treating obesity, hyperlipidemia, or metabolic disease, the method comprising administering a pharmaceutically effective amount of the butanol fraction of *Polygonum cuspidatum* or the ethylacetate fraction of *Polygonum cuspidatum* to an obese individual.

In Experimental example 4, it was found that administration of the butanol fraction of the *Polygonum cuspidatum* extract to high-fat diet-induced obese rats has actually the curative effect on obesity, hyperlipidemia, and metabolic diseases.

Individuals for which the treating method can be applicable may be vertebrates such as mice, which are supported in Examples. Preferably, individuals may be mammals, more preferably experimental animals such as rats, mice, rabbits, guinea pigs, hamsters, dogs, and cats, and most preferably anthropoids such as chimpanzees, gorillas, and humans.

In Examples of the present invention, the treating method for skin external use and the treating method by intraperitoneal injection are shown, but since the present invention has no cellular toxicity, in addition to the methods, oral or parenteral administration may be used for the treating method. For parenteral administration, intrarectal injection, intravenous injection, intramuscular injection, subcutaneous injection, epidural injection in uterine, or intracerebrovascular injection may be selected. The most preferable treating method may be used for skin external use, like Examples.

For the treating method, the administration dose of the pharmaceutical composition may be different depending on body weight, age, gender, health condition of patient, time of administration, method of administration, excretion rate, and severity of diseases to be treated.

The present invention provides also a method of preventing obesity, hyperlipidemia, or metabolic diseases, the method comprising administering a pharmaceutically effective amount of the *Polygonum cuspidatum* butanol fraction to an obese individual.

As shown in Experimental example 3, application of high-fat diet along with the butanol fraction of the *Polygonum cuspidatum* extract showed that the fraction of the present invention has the preventive effect on obesity, hyperlipidemia, or metabolic diseases. Thus, application of the butanol fraction of the *Polygonum cuspidatum* extract of the present invention to an ordinary individual may prevent obesity of the individual.

Furthermore, the present invention provides a use of a fraction for preparation of the composition for preventing or treating obesity, wherein the fraction is prepared by extracting *Polygonum cuspidatum* with water, an alcohol, or a mixed solvent thereof to obtain a *Polygonum cuspidatum* extract and further extracting the *Polygonum cuspidatum* extract with butanol or ethylacetate.

The butanol fraction or the ethylacetate fraction of the *Polygonum cuspidatum* extract of the present invention proved that it has the preventive and curative effect on obesity, hyperlipidemia, or metabolic diseases and thus the fraction of the present invention can be used for preparation of the pharmaceutical composition for treating the diseases.

EXAMPLE

Hereinafter, the present invention will be described in further detail with reference to the following examples and experimental examples.

Example 1

Preparation of *Polygonum cuspidatum* Water Extract

Rhizomes of *Polygonum cuspidatum* Sieb. et Zucc. (.=*Reynotria japonica* Houtt.; Polygonaceae) used in experiments were purchased from a herbal medicine shop Baekjedang in Daejeon province, Korea and identified by professor Kim Juhwan, Department of Life Science, Kyungwon University, Republic of Korea. A voucher specimen (no. KIOM-POCU1) has been deposited at the herbarium of Diabetic Complications Research Center, Korea Institute of Oriental Medicine.

300 mL of distilled water was added to the dried in the shade and finely cut *Polygonum cuspidatum* (30 g) and extraction was carried out three times repeatedly in an extraction vessel at room temperature for 2 h and water extract was obtained after filtration. The water extract was concentrated at 40° C. with a rotary vacuum concentrator. The concentrate was gone through vacuum drying, and finally, *Polygonum cuspidatum* water extract (2.5 g) was obtained.

Example 2

Preparation of *Polygonum cuspidatum* Ethanol Extract 6.8 kg of the dried in the shade and finely cut *Polygonum cuspidatum* was put into 36 L of ethanol and extracted in an extraction vessel three times for 24 h at room temperature and then concentrated at 40° C. under reduced pressure to obtain the ethanol extract. The ethanol extract was filtered and concentrated under reduced pressure. During concentration, the temperature was kept at 40 to 45° C. or lower in order to prevent decomposition and hydrolysis of constituents. Consequently, 580 g of the ethanol extract was obtained.

Example 3

Preparation of *Polygonum cuspidatum* Hexane Fraction

Figure 1:
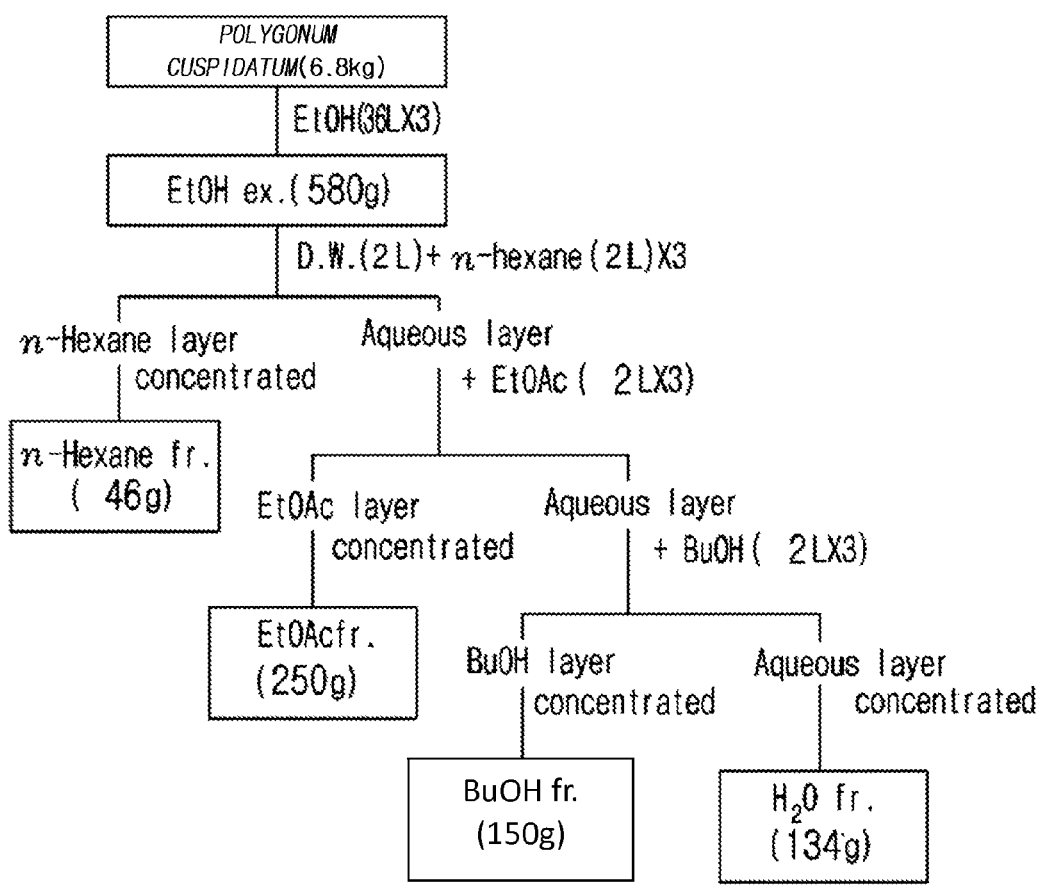
FIG. 1 shows extraction and systematic fractionation of *Polygonum cuspidatum*.

The *Polygonum cuspidatum* ethanol extract obtained in Example 2 was suspended in 2 L of distilled water and then extracted with 2 L of normal hexane (n-hexane) three times repeatedly to obtain 46 g of n-hexane layer, as shown in FIG. 1.

Example 4

Preparation of *Polygonum cuspidatum* Ethylacetate Fraction

The *Polygonum cuspidatum* ethanol extract obtained in Example 2 was suspended in 2 L of distilled water, and as shown in FIG. 1, the normal hexane layer and a water layer were separated using 2 L of normal hexane. The obtained water layer was extracted with 2 L of ethylacetate three times repeatedly to obtain 250 g of ethylacetate layer.

Example 5

Preparation of *Polygonum cuspidatum* Butanol Fraction

The *Polygonum cuspidatum* ethanol extract obtained in Example 2 was suspended in distilled water, and as shown in FIG. 1, systematic separation was successively carried out with normal hexane, ethylacetate (EtOAc), and normal butanol (n-BuOH). After concentration under reduced pressure and freeze-drying, 150 g of normal butanol fraction was obtained.

Example 6

Preparation of Resveratrol from the Ethylacetate Fraction of the *Polygonum* Ethanol Extract

*Polygonum* ethylacetate fraction (250 g) was applied to a silica gel column chromatography (70-230 mesh, ø 12×60 cm, methylene chloride/methanol=100:0→0:100) and divided into ten primary small fractions (F1 to F10). Among them, the fraction F5 (4.9 g) was applied to a medium pressure liquid chromatography using a mixed solvent of chloroform and methanol (chloroform 100%, 40 min; 98%, 30 min; 95%, 40 min; 90%, 60 min; Hi-Flash 2 L silica gel column, ø 12×60 cm, Yamazen YFLC AI-580, Japan) and trans-resveratrol was purely isolated and the structure was identified.

As described above, 180 mg of a monocompound was isolated and after analysis of spectral data ($^1$H-NMR, $^{13}$C-NMR), it was confirmed to be resveratrol ([Chemical Formula 1]).

Resveratrol—white powder, $^1$H-NMR (300 MHz, acetone-$d_6$) δ: 7.36 (2H, d, J=8.4 Hz, H-2'/H-6'), 7.02 (1H, d, J=16.4 Hz, H-8), 6.78 (2H, d, J=8.4 Hz, H-3'/H-5'), 6.74 (1H, d, J=16.4 Hz, H-7), 6.51 (2H, d, J=2.0 Hz, H-2/H-6), 6.25 (1H, t, J=2.0 Hz, H-4). $^{13}$C-NMR (75 MHz, acetone-$d_6$) δ: 159.6 (C-3'/C-5'), 158.2 (C-4), 141.0 (C-1'), 130.1 (C-1), 129.2 (C-8), 128.8 (C-2/C-6), 126.9 (C-7), 116.5 (C-3/C-5), 105.8 (C-2'/C-6'), 102.8 (C-4')

[Chemical Formula 1]

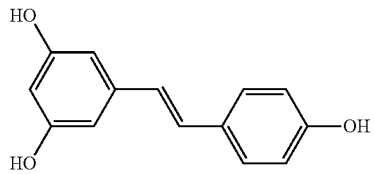

resveratrol, in vitro experiments on inhibition of porcine pancreatic lipase activity were carried out.

Experiments on inhibition of pancreatic lipase activity were measured using a porcine pancreatic lipase. First, 30 µL (10 units) of a porcine pancreatic lipase (Sigma, St. Louis, Mo., USA) which was mixed in an enzyme buffer (10 mM MOPS (morpholine propane sulphonic acid) and 1 mM EDTA, pH 6.8) and 850 µL of Tris buffer (100 mM TrisHCl and 5 mM $CaCl_2$, pH 7.0) were mixed to be prepared. Then, test materials at various concentrations and 100 µL of a positive control, orlistat (Roche, Basel, Switzerland), were mixed thereto and incubated for 15 min at 37° C. Then, 20 µL of the substrate solution (10 mM p-NPB (p-nitrophenyl-butyrate) in dimethylformamide) was added and further incubated for 15 min. Lipase activity was determined by measuring the hydrolysis of p-NPB to p-nitrophenol by lipase at 400 nm using an ELISA reader (BIO-TEK, Synergy HT, USA). Inhibition of lipase activity was expressed as the percentage decrease in optical density by the test materials and the concentration required to inhibit a lipase activity by 50% ($IC_{50}$) was calculated.

*Polygonum cuspidatum* ethanol extract, the hexane fraction of the *Polygonum cuspidatum* ethanol extract, the ethylacetate fraction, the butanol fraction, water extract, and resveratrol were prepared according to the above method, and experiments were carried out according to the above experimental example, and the inhibitory effect on pancreatic lipase activity was measured and the result was shown in Table 1.

TABLE 1

| | Concentration (µg/mL) Inhibitory effect on pancreatic lipase activity (%) | | | | $IC_{50}$ (µg/mL) |
|---|---|---|---|---|---|
| *Polygonum cuspidatum* water extract | 0<br>0 ± 4.75 | 200<br>43.0 ± 0.8 | 300<br>47.3 ± 2.5 | 400<br>51.8 ± 0.5 | 352.9 ± 16.5 |
| *Polygonum cuspidatum* ethanol extract | 0<br>0 ± 4.75 | 50<br>45.8 ± 1.9 | 100<br>54.9 ± 0.3 | 150<br>62.7 ± 3.2 | 72.5 ± 6.7 |
| Hexane fraction of *Polygonum cuspidatum* ethanol extract | 0<br>0 ± 4.75 | 200<br>33.9 ± 3.2 | 300<br>44.7 ± 7.3 | 400<br>64.1 ± 7.2 | 326.9 ± 36.6 |
| Ethylacetate fraction of *Polygonum cuspidatum* ethanol extract | 0<br>0 ± 4.75 | 20<br>44.6 ± 3.4 | 30<br>52.5 ± 0.7 | 40<br>54.1 ± 0.4 | 26.4 ± 1.9 |
| Butanol fraction of *Polygonum cuspidatum* ethanol extract | 0<br>0 ± 4.75 | 10<br>46.5 ± 0.3 | 15<br>49.7 ± 2.4 | 20<br>52.8 ± 1.4 | 15.8 ± 2.6 |
| Resveratrol | 0<br>0 ± 4.75 | 50<br>32.4 ± 3.0 | 100<br>47.2 ± 1.6 | 150<br>52.8 ± 1.6 | 124 ± 6.7 |

Experimental Example 1

Experiment on Inhibition of Pancreatic Lipase Activity

Using *Polygonum cuspidatum* ethanol extract, the hexane fraction of the *Polygonum cuspidatum* ethanol extract, the ethylacetate fraction, the butanol fraction, water extract, and As shown in Table 1, the inhibitory effect was arranged in order of excellence as follows: the butanol fraction of the *Polygonum cuspidatum* ethanol extract (15.8±2.6 µg/mL), the ethylacetate fraction (26.4±1.9 µg/mL), the ethanol extract (72.5±6.7 µg/mL), resveratrol (124±6.7 µg/mL), the hexane layer (326.9±36.6 µg/mL), and the water extract (352.9±16.5 µg/mL). The inhibitory effect of the butanol fraction was 4.6 times, 22 times, and 7.8 times more excellent that those of the ethanol extract, the water extract, and resveratrol. It was proved that the inhibitory effects of the ethylacetate fraction and the butanol fraction are far more excellent than those of *Polygonum cuspidatum* water extract or the ethanol extract.

Experimental Example 2

Analysis of the Inhibitory Effect on Short Term Absorption of Lipid Emulsions in Animals The inhibitory effect of the *Polygonum cuspidatum* ethanol extract, the hexane fraction of the *Polygonum cuspidatum* ethanol extract, the ethylacetate fraction, the butanol fraction, the water extract, and resveratrol on the extent of fat digestion and fat absorption in the intestinal tract of rat was measured.

fraction, the butanol fraction, the water extract, and resveratrol showed that as shown in Table 2, the amount of triglycerides increased twofold or more in the lipid emulsion only-administered group. However, obvious increases in triglycerides were not shown in the *Polygonum cuspidatum* butanol fraction-administered group and the *Polygonum cuspidatum* ethylacetate fraction-administered group.

For the groups administered 250 mg of each drug, the inhibitory effect on fat absorption was arranged in order of excellence as follows: the butanol fraction (140.1±32.4 mg/dL), the ethylacetate fraction (170.1±32.4 mg/dL), the water extract (191.3±23.1 mg/dL), the ethanol extract (194.4±18.8 mg/dL), and resveratrol (228.5±8.4 mg/dL).

That is, it was proved that the inhibitory effects of the butanol fraction and the ethylacetate fraction are more excellent than those of the *Polygonum cuspidatum* ethanol extract, the water extract, and resveratrol (Table 2).

TABLE 2

| | | Concentration of serum triglyceride (mg/dL) Time (Hour) | | | | |
|---|---|---|---|---|---|---|
| | | 0 | 1 | 2 | 3 | 4 |
| Negative control | | 154.8 ± 25.6 | 121.9 ± 8.8 | 115.4 ± 16.2 | 108.9 ± 9.0 | 100.0 ± 9.36 |
| Positive control | | 160.9 ± 23.6 | 179.7 ± 24.8 | 242.6 ± 27.8 | 195.2 ± 28.4 | 189.8 ± 23.9 |
| Xenical | | 159.6 ± 19.0 | 133.7 ± 11.3 | 124.4 ± 18.0 | 118.1 ± 24.5 | 120.9 ± 12.5 |
| Polygonum cuspidatum water extract | 100 mg/kg | 145.0 ± 27.6 | 198.2 ± 22.5 | 191.6 ± 42.0 | 169.5 ± 55.6 | 180.2 ± 55.5 |
| | 250 mg/kg | 146.1 ± 31.7 | 179.4 ± 14.2 | 191.3 ± 23.1 | 179.7 ± 20.3 | 174.8 ± 12.3 |
| Polygonum cuspidatum ethanol extract | 100 mg/kg | 149.6 ± 8.3 | 130.8 ± 8.2 | 218.0 ± 52.2 | 219.8 ± 62.4 | 194.2 ± 19.6 |
| | 250 mg/kg | 150.0 ± 35.3 | 144.1 ± 37.5 | 194.4 ± 18.8 | 188.7 ± 61.6 | 157.0 ± 97.9 |
| Ethylacetate fraction of Polygonum cuspidatum ethanol extract | 100 mg/kg | 157.8 ± 25.5 | 141.2 ± 44.8 | 192.7 ± 26.8 | 175.0 ± 29.5 | 162.6 ± 20.4 |
| | 250 mg/kg | 161.5 ± 29.5 | 157.0 ± 36.8 | 170.1 ± 32.4 | 145.3 ± 21.2 | 142.2 ± 34.3 |
| Butanol fraction of Polygonum cuspidatum ethanol extract | 100 mg/kg | 147.8 ± 25.5 | 151.2 ± 44.8 | 140.7 ± 26.8 | 155.0 ± 29.5 | 162.6 ± 20.4 |
| | 250 mg/kg | 151.5 ± 29.5 | 140.0 ± 36.8 | 140.1 ± 32.4 | 130.3 ± 21.2 | 122.2 ± 34.3 |
| Resveratrol | 10 mg/kg | 147.0 ± 4.2 | 212.5 ± 14.0 | 219.3 ± 77.3 | 195.5 ± 25.9 | 193.2 ± 12.1 |
| | 50 mg/kg | 146.1 ± 1.4 | 208.3 ± 31.0 | 228.0 ± 58.4 | 198.8 ± 62.3 | 183.7 ± 50.3 |

4-week-old male wistar rats (Orient Bio, Korea) were acclimated for 1 week. All animals were fasted for 18 h before the experiment and 3 mL of lipid emulsions (3 mL corn oil, 50 mg cholic acid, 3 mL saline and 1 g cholestryl oleate) and 100 mg/kg and 250 mg/kg of the *Polygonum cuspidatum* ethanol extract, the hexane fraction of the *Polygonum cuspidatum* ethanol extract, the ethylacetate fraction, the butanol fraction, the water extract, and resveratrol were administered orally. For a negative control, only the same amount of saline was administered. For a drug control, 200 mg/kg of orlistat (Roche, Basel, Switzerland) was administered. Blood samples were taken from the caudal vein before administration and 1 h, 2 h, 3 h, 4 h after administration of each drug. Collected bloods were centrifuged at 5,500 g for 5 min and then plasma was separated. Concentration of plasma triacylglyceride was measured using Wako Triglyceride E-test kit.

Experiments on the inhibitory effect on short term fat absorption by administering lipid emulsions and the *Polygonum cuspidatum* ethanol extract, the hexane fraction of the *Polygonum cuspidatum* ethanol extract, the ethylacetate The above [Table 2] shows the inhibitory effect on short term absorption of lipid emulsions of the *Polygonum cuspidatum* ethanol extract; each fraction from the hexane layer of the *Polygonum cuspidatum* extract, the ethylacetate layer, the butanol layer, and the water layer; the water extract; and resveratrol in animals.

Experimental Example 3

Anti-Obesity Effect Marker, Anti-Lipogenetic Effect

The inhibitory effect on body weight gain and effects on lipogenesis, fatty liver, hyperlipidemia, and insulin secretion of the *Polygonum cuspidatum* butanol fraction (hereinafter, referred to as "POCU-1b") were evaluated.

For experimental animals, 3-week-old male C57BL/6 mice were prepared and fed a high-fat diet to induce obesity. AIN76A diet (AIN76A based 45 Kcal % High fat diet, Research Diets, Inc. USA, D12451, calorie composition: fat 45%, carbohydrates 35%, protein 20%) was used for a high-fat diet, Purina Rodent Chow was used for a normal diet. The animals were allowed to access freely to feeds and drinking water. The test drug POCU was mixed with the high-fat feed in an amount of 0.1% and 1%, and the control drug Xenical was mixed with the feed in an amount of 0.1% to be supplied. During 10 weeks, high fat feeds mixed with drugs were supplied to induce obesity and changes in body weight were analyzed at each week. After 10 weeks, autopsy was carried out and fats, livers, pancreas, muscles, etc. were removed for analysis of the effects of drugs.

<3-1> Observation on Changes in Body Weight

The body weights in the group administered a high-fat diet only have steadily increased, however, the body weight gain was significantly inhibited in the group wherein 1% of POCU-1b was mixed (*p<0.01) (FIG. 2). The extent of body weight gain was 10.9 g in the high-fat diet-administered group, 6.1 g in the Xenical-administered group, and 3.6 g in the POCU-1b-administered group. Thus, the preventive effect on body weight gain of the POCU-1b was more excellent than that of Xenical ($, *p<0.01) (FIG. 3).

<3-2> Observation on the Preventive Effect on Increase in Fats from Each Body Part In order to analyze whether adipose tissues increase or not, gonadal fat (left/right), perirenal fat (left/right), subcutaneous fat (left/right), and brown fat were carefully removed and washed with physiological saline, and then water was removed using a filter paper, and the weights of adipose tissues were measured.

The POCU-1 administered group (1% POCU-1 mixed group) prevented increase in fats from each body part excellently (subcutaneous fat: 0.15 g, gonadal fat: 0.21 g, perirenal fat: 0.07 g). The effect was excellent similarly to that of the monocompound Xenical (subcutaneous fat: 0.14 g, gonadal fat: 0.17 g, perirenal fat: 0.04 g) (*P<0.01) (FIGS. 4, 5 and 6).

<3-3> Observation on the Inhibitory Effect on Adipocyte Size

Removed adipose tissues were fixed in 10% formalin, paraffin embedded, and slides were prepared. Slides were stained with H&E and adipocyte size was analyzed under an optical microscope. As shown in FIG. 7, adipocyte size of the high-fat diet group increased remarkably (125 μm), however, that of the POCU-1b-administered group was kept within the normal range (61 μm) and the effect of the POCU-1b-administered group was more excellent than that of Xenical (75 μm) (#p<0.01) (FIG. 7).

<3-4> Observation on the Effect on Anti-Hyperlipidemia

After test was over, experimental animals were fasted for 16 h. Blood was collected at autopsy from the aorta ventralis and centrifuged at 3,000 rpm for 10 min to separate serum and plasma. Using the separated serum, fat metabolism-related markers, that is, triglyceride, high density lipoprotein (HDL), low density lipoprotein (LDL), and total cholesterol were measured with the serum auto-analyzer (Hitachi 7060, Japan).

As a result, the amounts of total cholesterol, triglyceride, LDL, and free fatty acids increased significantly by 183%, 161%, 267%, and 114% or more respectively in the high-fat-diet group. However, the amounts of total cholesterol (29%), triglyceride (22%), LDL (32%), and free fatty acids (32%) decreased significantly in the POCU-1b (1%)-administered group and it was proved that the effect of POCU-1b is good (FIGS. 9 to 13).

<3-5> The Preventive Effect on Fatty Liver

As fat increases, fat accumulates in the liver and fatty liver develops. When fatty liver develops, the original color of the liver, reddish color disappears due to the accumulated fat.

As shown in FIG. 14, the color of the liver in the POCU-1b (1%)-administered group remained the same reddish to that of the normal group (FIG. 14). This means that the administration of POCU-1b (1%) prevented the accumulation of fats in the liver.

As a result of analyzing the amount of triglyceride in the liver, the administration of POCU-1b (0.1%, 1.0%) prevented significantly the increase in triglyceride by 33% and 40%, respectively (#p<0.01) (FIG. 15).

Liver tissues collected at autopsy were fixed in 10% neutralized formalin and processed. Tissues were stained with hematoxylin & eosin and observed under an optical microscope. As a result of staining liver tissues, liver tissues centered around a central vein were well observed in the normal group, while liver tissues in the high-fat diet group changed remarkably due to excessive accumulation of fat. However, liver tissues in the POCU-1b (1%)-administered group showed almost the same appearance to liver tissues in the normal group (FIG. 16). This proves that the administration of POCU-1b (1%) prevented fatty liver complications.

<3-6> Observation on the Preventive Effect on Insulin-Resistance

Obesity induces insulin resistance and moves forward to diabetes, automatically. It was proved that the administration of POCU-1b (1%) prevented insulin resistance significantly (#p<0.01) (FIG. 17).

At the same time, beta cells, the cells that secrete insulin in the pancreas, were analyzed. Almost all beta cells in the high-fat diet group were damaged, while the almost same beta cells in the normal group were observed a lot in the POCU-1b (1%)-administered group (FIG. 18). From this, it was proved that POCU-1b (1%) prevents the disruption of beta cells, thereby preventing serum insulin resistance.

<3-7> Changes in the Expression of the Lipogenesis Marker aP2 mRNA was extracted from liver tissues and RT-PCR was carried out using the adipogenesis marker, aP2 primer. As shown in FIG. 19, when the lipogenesis marker, aP2 mRNA was analyzed through RT-PCR, aP2 marker from the high-fat diet group increased by 1.4 times or more, but aP2 marker from the POCU-1b (1%)-administered group decreased significantly within the normal range (*p<0.01). This means that the lipogenesis by the high-fat diet was prevented by POCU-1b.

Experimental Example 4

The Effect of POCU-1b on Lipolysis (The obesity-curative effect of POCU-1b)

4-1> Observation on Body Weight Reduction

In order to evaluate the effect of POCU-1b on body weight reduction and lipolysis in high-fat diet-induced obese rats, high-fat diet was fed to rats for 10 weeks before the administration of drugs to induce extreme obesity and then POCU-1b (0.1%, 1.0%) was administered and changes in body weight were observed. The administration of POCU-1b (1%) showed the more excellent curative effect on body weight reduction than Xenical (*,p<0.01) (FIG. 20**).

<4-2> Observation on the Preventive Effect on Increase in Fats from Each Body Part As shown in FIGS. 21 to 24, fat weight from each body part was measured. Genital fat from the high-fat diet group was about 11 g and increased by about two-fold compared to 6.2 g in the normal group. However, genital fat from the POCU-1b (1%)-administered group was 6.3 g and decreased significantly (p<0.01). In cases of perirenal fat and subcutaneous fat, the same results showed as in case of genital fat and in case of brown fat, significant fat weight reduction was observed in both the POCU-1b (0.1%)-administered group and the POCU-1b (1.0%)-administered group (p<0.01).

<4-3> Observation on the Inhibitory Effect on Adipocyte Size

Adipose tissues which were removed at autopsy were fixed in 10% neutral formalin, paraffin embedded, and slides were prepared. Slides were stained with H&E and adipocyte size was analyzed under an optical microscope.

As shown in FIGS. 25 and 26, adipocyte size of the high-fat diet group increased remarkably (79 μm), however, that of the POCU-1b-administered group was kept within the normal range (56 μm) (#p<0.01).

<4-4> The Effect on Anti-Hyperlipidemia

After test was over, experimental animals were fasted for 16 h. Blood was collected at autopsy from the aorta ventralis and centrifuged at 3,000 rpm for 10 min to separate serum and plasma. Using the separated serum, fat metabolism-related markers, that is, triglyceride, high density lipoprotein (HDL), low density lipoprotein (LDL), and total cholesterol were measured with the serum auto-analyzer (Hitachi 7060, Japan).

As a result, total cholesterol, triglyceride, and LDL increased significantly by 144%, 171%, and 135% or more respectively, and HDL decreased by 9% in the high-fat-diet group. However, the amounts of total cholesterol (27%), triglyceride (65%), and LDL (36%) decreased significantly in the POCU-1b (1%)-administered group and it was proved that the effect of POCU-1b is good. The amount of HDL increased significantly by 127% and 121%, respectively by the administration of POCU-1b (0.1%, 1.0%) (#p<0.05) (FIGS. 27 to 30).

<4-5> The Curative Effect on Fatty Liver

As fat increases, fat accumulates in the liver and fatty liver develops. When fatty liver develops, the original color of the liver, reddish color disappears due to the accumulated fat.

As shown in FIG. 31, the color of the liver in the POCU-1b (1%)-administered group remained the same reddish to that of the normal group (FIG. 31). This means that the administration of POCU-1b (1%) prevented the accumulation of fats in the liver.

As a result of analyzing the liver weight, it was found that the increase in triglyceride was treated significantly by the administration of POCU-1b (0.1%, 1.0%) (#p<0.01) (FIG. 32).

At the same time, liver tissues collected at autopsy were fixed in 10% neutralized formalin and processed. Tissues were stained with H&E and observed under an optical microscope. As a result of staining liver tissues, liver tissues centered around a central vein were well observed in the normal group, while liver tissues in the high-fat diet group changed remarkably due to excessive accumulation of fat. However, liver tissues in the POCU-1b (1%)-administered group showed almost the same appearance to liver tissues in the normal group (FIG. 33). This proves that fatty liver complications were treated by the administration of POCU-1b (1%).

As a result of analyzing the amount of triglyceride in the liver, the increase in triglyceride was treated significantly by the administration of POCU-1b (0.1%, 1.0%) (#p<0.05) (FIG. 34).

<4-6> The Curative Effect on Obesity-Induced Insulin Resistance

The effect of POCU-1b on changes in the expression of IL-6, TNF-α, and SOSC-3 (suppressor of cytokine signalling-3), which are key enzymes for insulin metabolism, was analyzed in the liver and serum. It has been widely known that obesity causes insulin resistance, and therefore, causes severe diabetes (complications). Due to obesity, IL-6, TNF-α, adiponectin, etc. work abnormally and cause insulin resistance through SOCS (suppressors of cytokine signaling) pathway and TSC/mTOR pathway in liver or muscle.

Concentrations of IL-6 and TNF-α, which are blood adipocytokines, were evaluated with ELISA and concentrations of these proteins in adipocyte were evaluated with Western blot.

Concentrations of these adipocytokines increased 1.4 times in the high-fat diet group, while the increased concentrations of serum IL-6 and serum TNF-α were restored to the normal level by the administration of POCU-1b (1%) (FIG. 35 and FIG. 36).

In addition, changes in adipocytokines, IL-6 and TNF-α proteins in the adipose tissue as well as in blood were restored to the normal level, and thus, the curative effect was proved (FIG. 37 and FIG. 38).

At the same time, blood glucose, serum insulin resistance, HbA1c, insulin sensitivity, and HOMA index were restored to the normal level by POCU-1b (FIGS. 39 to 43).

In order to observe changes in beta cells which make insulin in the pancreas, immunohistochemical staining was carried out using anti-insulin antibody (Abcam, USA).

Enlargement of beta cells and disappearance of insulin were observed in the high-fat diet group, while the morphology of beta cells and the amount of insulin were normal in the POCU-1b administered group (FIG. 44).

In order to examine whether the improvement of insulin resistance by POCU-1b is mediated through SOCS and NF-κB signaling pathway, Western blot analysis for SOSC and NF-kB ELISA-based DNA binding assay were carried out. Consequently, it was found that the improvement of insulin resistance by POCU-1b was thanks to a mechanism which restores the SOSC level and NF-κB activity to the normal level (FIG. 45 and FIG. 46).

<4-7> The Effect on Fat Metabolism in the Muscle and Liver Tissue

The ideal fat metabolism is that the balance between lipogenesis and lipolysis is appropriately maintained. However, excessive intake of nutrients through foods breaks this fat metabolic balance and causes the accumulation of excessive fat in the muscle and liver tissue. The effect of POCU-1b on the imbalance of fat metabolism was examined.

There are various factors which affect fat metabolism and among them, concentrations of adiponectin and leptin, which are adipocyte-secreted serum adipocytokines, were measured by ELISA. As shown in FIG. 47 and FIG. 48, the concentration of serum adiponectin decreased 0.7 times in the high-fat diet group, whereas the concentration of serum leptin increased about 2.5 times. However, the concentrations of serum adiponectin and leptin were recovered to the normal level in the POCU-1b (1%)-administered group (FIG. 47 and FIG. 48).

Moreover, proteins and mRNA were extracted from liver tissues, where fats are mainly accumulated, and the expression amounts of adenosine monophosphate activated protein kinase (AMPK) and acetyl-CoA carboxylase (ACC), which are important factors involving in fat metabolism, and fatty acid synthase (FAS) were analyzed.

As shown in FIGS. 49, 50, and 51, the expression amounts of p-AMPK (phospho-AMP-kinase) and AMPK decreased about 10% in the high-fat diet group, however, those were recovered to the normal level by the administration of POCU-1b (1%).

As shown in FIG. 52, the expression amount of ACC decreased about 23% in the high-fat diet group, however, that was recovered to the normal level in the POCU-1b (1%)-administered group.

Meanwhile, the expression amount of FAS mRNA increased about 150% in the high-fat diet group, and it decreased in a concentration-dependent manner by the administration of POCU-1b (FIG. 53).

In order to measure the activity of carnitine palmitoyl transferase 1 (CPT-1), an important enzyme involving in fat oxidation in tissues, proteins were extracted from liver tissues and the activity was measured using nitrophenyl butyrate as a substrate.

As shown in FIG. 54, the activity of CPT-1, which is related with fat oxidation, was decreased significantly by about 58% due to the high-fat diet, however, it was recovered to the normal level by the administration of POCU-1b (1%).

Through the above research results, it was proved that the anti-obesity effect of the *Polygonum cuspidatum* ethylacetate fraction and the butanol fraction is excellent in inhibiting pancreatic lipase activity, inhibiting intestinal fat absorption, inhibiting body weight gain, and reducing body weight. The *Polygonum cuspidatum* ethylacetate fraction and the butanol fraction can be used as a new therapeutic agent for diseases such as obesity, hyperlipidemia, and metabolic diseases.

INDUSTRIAL APPLICABILITY

The present invention is effective in inhibiting pancreatic lipase activity and has inhibitory effect on fat absorption in intestinal tract, and thus, the present invention is an effective natural extract for treating and preventing obesity. The present invention can be used not only pharmaceutically as a composition for treating and preventing obesity, but also as a health functional food.

The invention claimed is:

1. A method of treating obesity comprising:
   administering a pharmaceutical composition comprising an effective amount of a butanol fraction of *Polygonum cuspidatum* to a subject in need thereof,
   wherein
   the butanol fraction is obtained by:
   i) extracting *Polygonum cuspidatum* with ethanol to prepare an ethanol extract of *Polygonum cuspidatum;*
   ii) partitioning the ethanol extract of *Polygonum cuspidatum* obtained from step i) with hexane and water to provide a hexane layer and a water layer;
   iii) separating the water layer to obtain a first aqueous layer;
   iv) extracting the first aqueous layer obtained from step iii) with ethyl acetate to obtain an ethyl acetate layer and a second aqueous layer; and
   v) separating the second aqueous layer from the ethyl acetate layer and extracting the second aqueous layer with butanol to provide the butanol fraction.

2. A method of treating hyperlipidemia comprising:
   administering a pharmaceutical composition comprising an effective amount of a butanol fraction of *Polygonum cuspidatum* to a subject in need thereof,
   wherein the butanol fraction is obtained by:
   i) extracting *Polygonum cuspidatum* with ethanol to prepare an ethanol extract of *Polygonum cuspidatum;*
   ii) partitioning the ethanol extract of *Polygonum cuspidatum* obtained from step i) with hexane and water to provide a hexane layer and a water layer;
   iii) separating the water layer to obtain a first aqueous layer;
   iv) extracting the first aqueous layer obtained from step iii) with ethyl acetate to obtain an ethyl acetate layer and a second aqueous layer; and
   v) separating the second aqueous layer from the ethyl acetate layer and extracting the second aqueous layer with butanol to provide the butanol fraction.

3. A method of treating lipid metabolic syndrome comprising:
   administering a pharmaceutical composition comprising an effective amount of a butanol fraction of *Polygonum cuspidatum* to a subject in need thereof,
   wherein
   the butanol fraction is obtained by:
   i) extracting *Polygonum cuspidatum* with ethanol to prepare an ethanol extract of *Polygonum cuspidatum;*
   ii) partitioning the ethanol extract of *Polygonum cuspidatum* obtained from step i) with hexane and water to provide a hexane layer and a water layer;
   iii) separating the water layer to obtain a first aqueous layer;
   iv) extracting the first aqueous layer obtained from step iii) with ethyl acetate to obtain an ethyl acetate layer and a second aqueous layer; and
   v) separating the second aqueous layer from the ethyl acetate layer and extracting the second aqueous layer with butanol to provide the butanol fraction.

* * * * *